(12) United States Patent
Pallem et al.

(10) Patent No.: US 9,087,690 B2
(45) Date of Patent: Jul. 21, 2015

(54) HAFNIUM-CONTAINING AND ZIRCONIUM-CONTAINING PRECURSORS FOR VAPOR DEPOSITION

(75) Inventors: Venkateswara R. Pallem, Hockessin, DE (US); Christian Dussarrat, Tokyo (JP)

(73) Assignee: American Air Liquide, Inc., Fremont, CA (US)

( * ) Notice: Subject to any disclaimer, the term of this patent is extended or adjusted under 35 U.S.C. 154(b) by 3 days.

(21) Appl. No.: 14/009,812

(22) PCT Filed: Apr. 6, 2011

(86) PCT No.: PCT/US2011/031360
§ 371 (c)(1),
(2), (4) Date: Dec. 10, 2013

(87) PCT Pub. No.: WO2012/138332
PCT Pub. Date: Oct. 11, 2012

(65) Prior Publication Data
US 2014/0170861 A1 Jun. 19, 2014

(51) Int. Cl.
*H01L 21/02* (2006.01)
*C07F 7/00* (2006.01)
*C23C 16/40* (2006.01)

(52) U.S. Cl.
CPC .......... *H01L 21/02181* (2013.01); *C07F 7/006* (2013.01); *C23C 16/405* (2013.01); *H01L 21/0228* (2013.01); *H01L 21/02189* (2013.01)

(58) Field of Classification Search
CPC . C07F 7/006; C23C 16/405; H01L 21/02181; H01L 21/02189; H01L 21/0228
USPC ...................................... 556/55, 56; 438/785
See application file for complete search history.

(56) References Cited

U.S. PATENT DOCUMENTS

| | | | |
|---|---|---|---|
| 6,821,921 | B2 | 11/2004 | Theopold et al. |
| 7,491,654 | B2 | 2/2009 | Song et al. |
| 7,605,094 | B2 * | 10/2009 | Lee et al. ................. 438/785 |
| 2005/0277223 | A1 | 12/2005 | Lee et al. |
| 2008/0280455 | A1 | 11/2008 | Quick |
| 2009/0275199 | A1 | 11/2009 | Millward et al. |
| 2010/0003532 | A1 | 1/2010 | Feist et al. |
| 2010/0112211 | A1 | 5/2010 | Xu et al. |

FOREIGN PATENT DOCUMENTS

| | | |
|---|---|---|
| JP | 2006 45083 | 2/2006 |
| KR | 10 0584200 | 8/2005 |
| KR | 10 0640654 | 11/2006 |
| KR | 2010 0016477 | 2/2010 |
| WO | WO 2006 012052 | 2/2006 |

OTHER PUBLICATIONS

Alluri, P. et al., "ECR-MOCVD of the Ba-Sr-Ti-O system below 400° C * Part I: Processing," Integrated Ferroelectrics, 1998, vol. 21, pp. 305-318.
Anonymous, "Zirconium and hafnium amidinates metal-organic compounds and method of forming hafnium and zirconium containing thin films using the same," published on Aug. 10, 2007 at http://www.ip.com, publication No. IPCOM000157034D.
Bedoya, C. et al., "MOCVD of Sr-containing oxides: Transport properties and deposition mechanisms of the Sr(tmhd)$_2$.pmdeta precursor," Chem. Vap. Deposition 2005, 11, pp. 269-275.
Blanquart, T. et al., "Novel heteroleptic precursors for atomic layer deposition of TiO$_2$," Chem. Mater. 2012, 24(17), pp. 3420-3424.
Chen, X-Q et al., "Reaction of titanium tetrabutoxide with acetic anhydride and structure analysis of the titanyl organic compounds products," Acta Chimica Sinica, 2003, 61(10), pp. 1592-1596.
Cotton, S.A., "Titanium, zirconium and hafnium," Annu. Rep. Prog. Che., Sect. A, Aug. 9, 2001, vol. 97, pp. 133-142.
Durand, H.-A. et al., "Excimer laser sputtering deposition of TiO$_2$ optical coating for solar cells," Applied Surface Science 86 (1995) pp. 122-127.
Hwang, C.S. et al., "Deposition and electrical characterization of very thin SrTiO$_3$ films for ultra large scale integrated dynamic random access memory application," Japan Journal of Applied Physics, vol. 34 (1995) p. 5178-5183.
Inoue, T. et al., "Photoelectrocatalytic reduction of carbon dioxide in aqueous suspensions of semiconductor powders," Nature, vol. 277, Feb. 22, 1979, pp. 637-638.
Katamreddy, R. et al., "Ti source precursors for atomic layer deposition of TiO$_2$, STO and BST," 2008 ECS conference.
Keshmiri, M. et al., "Apatite formation on TiO$_2$ anatase microspheres," Journal of Non-Crystalline Solids 324 (2003) pp. 289-294.
Kim, H. et al., "Laser processing of nanocrystalline TiO$_2$ films for dye-sensitized solar cells," Applied Physics Letters, vol. 85, No. 3, Jul. 19, 2004, pp. 464-466.
Scott, J.F. et al., "Ferroelectric memories," Science, vol. 246, Dec. 15, 1989, pp. 1400-1405.
Wang, C.-W. et al., "Gamma-ray-irradiation effects on the leakage current and reliability of sputtered TiO$_2$ gate oxide in metal-oxide-semiconductor capacitors," Journal of Applied Physics, vol. 91, No. 11, Jun. 1, 2002, pp. 9198-9203.
Zhang, Y. et al., "Unexpected carbon-oxygen bond cleavage of THF promoted by guanidinate titanium complex/lithium diisopropylamide: Synthesis and crystal structure," Chinese Science Bulletin (2005), 50(24), pp. 2817-2820.
International Search Report and Written Opinion for PCT/US2011/031346, Oct. 20, 2011.
International Search Report and Written Opinion for corresponding PCT/US2011/031360, Dec. 14, 2011.

* cited by examiner

*Primary Examiner* — Porfirio Nazario Gonzalez
(74) *Attorney, Agent, or Firm* — Patricia E. McQueeney

(57) ABSTRACT

Disclosed are hafnium-containing and zirconium-containing precursors and methods of synthesizing the same. The compounds may be used to deposit hafnium, zirconium, hafnium oxide, and zirconium oxide containing layers using vapor deposition methods such as chemical vapor deposition or atomic layer deposition.

19 Claims, No Drawings

HAFNIUM-CONTAINING AND ZIRCONIUM-CONTAINING PRECURSORS FOR VAPOR DEPOSITION

CROSS REFERENCE TO RELATED APPLICATIONS

This application is a 371 of International PCT Application PCT/US2011/031360, filed Apr.6, 2011, the entire contents of which are incorporated herein by reference.

TECHNICAL FIELD

Disclosed are hafnium-containing and zirconium-containing precursors, methods of synthesizing the same, and methods of using the same to deposit hafnium-containing and zirconium-containing layers using vapor deposition processes.

BACKGROUND

One of the serious challenges the semiconductor industry faces is developing new gate dielectric materials for DRAM and capacitors. For decades, silicon dioxide ($SiO_2$) was a reliable dielectric, but as transistors have continued to shrink and the technology has moved from "Full Si" transistors to "Metal Gate/High-k" transistors, the reliability of the $SiO_2$-based gate dielectric is reaching its physical limits. The need for new high dielectric constant materials and processes is increasing and becoming more and more critical as the size for current technology shrinks.

US Pat App Pub No 2005/277223 discloses ALD methods of forming metal oxides using metal-containing precursors having the formula $M(L1)_x(L2)_y$, wherein M is a metal, L1 and L2 may be halide, diketonate, alkoxide, amino, alkoxyamine, amidinate, or multidentate ligands. The exemplary precursors however are only $Hf(OtBu)_2(NEtMe)_2$, $Hf(OtBu)_2(NEt_2)_2$, $Hf(NEt_2)_2(DMAMP)_2$, $Hf(NEtMe)_2(DMAMP)_2$, $Ti(OtBu)_3Cl$, $Ti(OtBu)_3Me$, $Ti(OtBu)_2(NEt_2)_2$, $Ti(NEt_2)_2(DMAMP)_2$, $Ti(OtBu)_2(DMAMP)_2$, and $TiCl_2(DMAMP)_2$.

U.S. Pat. No. 7,491,654 discloses ALD methods of forming $ZrO_2$ thin films using a tris(N-ethyl-N-methylamino)(tertbutoxy)zirconium precursor.

Other sources and methods of incorporating Hf-containing and Zr-containing materials are being sought for new generations of integrated circuit devices. Novel precursors are needed.

SUMMARY

Disclosed are molecules having the following formula:

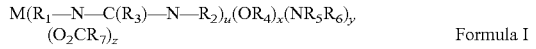

Formula I or

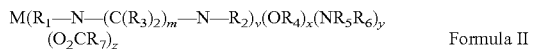

Formula II wherein:
M is Hf or Zr;
$R_1$, $R_2$, $R_5$, $R_6$, and $R_7$ are independently selected from the group consisting of H and C1-C6 alkyl group;
$R_3$=H, C1-C6 alkyl group, or $NMe_2$;
$R_4$ is a C1-C6 alkyl group;
m=2-4;
u=0-2;
v=0-1;
x=1-3;
y=0-2;
z=0-1;
in Formula I, u+x+y+z=4;
in Formula II, 2v+x+y+z=4; and u, v, or z The disclosed molecules may further include one or more of the following aspects:
the molecule having Formula I, wherein u=1, x=3, y=0, and z=0;
the molecule being selected from the group consisting of M(iPr-N—C(Me)-N-iPr)$_1$(OiPr)$_3$, M(iPr-N—C(Me)-N-iPr)$_1$(OMe)$_3$, M(iPr-N—C(Me)-N-iPr)$_1$(OEt)$_3$, M(iPr-N—C(Me)-N-iPr)$_1$(OnPr)$_3$, M(iPr-N—C(Me)-N-iPr)$_1$(OsBu)$_3$, M(iPr-N—C(Me)-N-iPr)$_1$(OiBu)$_3$, M(iPr-N—C(Me)-N-iPr)$_1$(OtBu)$_3$, M(Et-N—C(Me)-N-Et)$_1$(OEt)$_3$, M(Et-N—C(Me)-N-Et)$_1$(OMe)$_3$, M(Et-N—C(Me)-N-Et)$_1$(OnPr)$_3$, M(Et-N—C(Me)-N-Et)$_1$(OsBu)$_3$, M(Et-N—C(Me)-N-Et)$_1$(OiBu)$_3$, M(Et-N—C(Me)-N-Et)$_1$(OtBu)$_3$, and M(iPr-N—C(NMe$_2$)—N-iPr)(OiPr)$_3$;
the molecule having Formula II, wherein v=1, x=2, y=0, and z=0;
The molecule being selected from the group consisting of M(iPr-N—(CH$_2$)$_2$—N-iPr)$_1$(OiPr)$_2$, M(iPr-N—(CH$_2$)$_2$—N-iPr)$_1$(OMe)$_2$, M(iPr-N—(CH$_2$)$_2$—N-iPr)$_1$(OEt)$_2$, M(iPr-N—(CH$_2$)$_2$—N-iPr)$_1$(OnPr)$_2$, M(iPr-N—(CH$_2$)$_2$—N-iPr)$_1$(OsBu)$_2$, M(iPr-N—(CH$_2$)$_2$—N-iPr)$_1$(OiBu)$_2$, M(iPr-N—(CH$_2$)$_2$—N-iPr)$_1$(OtBu)$_2$, M(Et-N—(CH$_2$)$_2$—N-Et)$_1$(OiPr)$_2$, M(Et-N—(CH$_2$)$_2$—N-Et)$_1$(OMe)$_2$, M(Et-N—(CH$_2$)$_2$—N-Et)$_1$(OEt)$_2$, M(Et-N—(CH$_2$)$_2$—N-Et)$_1$(OnPr)$_2$, M(Et-N—(CH$_2$)$_2$—N-Et)$_1$(OsBu)$_2$, M(Et-N—(CH$_2$)$_2$—N-Et)$_1$(OiBu)$_2$, M(Et-N—(CH$_2$)$_2$—N-Et)$_1$(OtBu)$_2$, M(iPr-N—(CH$_2$)$_3$—N-iPr)$_1$(OiPr)$_2$, M(iPr-N—(CH$_2$)$_3$—N-iPr)$_1$(OMe)$_2$, M(iPr-N—(CH$_2$)$_3$—N-iPr)$_1$(OEt)$_2$, M(iPr-N—(CH$_2$)$_3$—N-iPr)$_1$(OnPr)$_2$, M(iPr-N—(CH$_2$)$_3$—N-iPr)$_1$(OsBu)$_2$, M(iPr-N—(CH$_2$)$_3$—N-iPr)$_1$(OiBu)$_2$, M(iPr-N—(CH$_2$)$_3$—N-iPr)$_1$(OtBu)$_2$, M(Et-N—(CH$_2$)$_3$—N-Et)$_1$(OiPr)$_2$, M(Et-N—(CH$_2$)$_3$—N-Et)$_1$(OMe)$_2$, M(Et-N—(CH$_2$)$_3$—N-Et)$_1$(OEt)$_2$, M(Et-N—(CH$_2$)$_3$—N-Et)$_1$(OnPr)$_2$, M(Et-N—(CH$_2$)$_3$—N-Et)$_1$(OsBu)$_2$, M(Et-N—(CH$_2$)$_3$—N-Et)$_1$(OiBu)$_2$, and M(Et-N—(CH$_2$)$_3$—N-Et)$_1$(OtBu)$_2$;
the molecule having Formula I, wherein u=2, x=2, y=0, and z=0;
the molecule being selected from the group consisting of M(iPr-N—C(H)—N-iPr)$_2$(OiPr)$_2$, M(iPr-N—C(H)—N-iPr)$_2$(OMe)$_2$, M(iPr-N—C(H)—N-iPr)$_2$(OEt)$_2$, M(iPr-N—C(H)—N-iPr)$_2$(OnPr)$_2$, M(iPr-N—C(H)—N-iPr)$_2$(OsBu)$_2$, M(iPr-N—C(H)—N-iPr)$_2$(OiBu)$_2$, M(iPr-N—C(H)—N-iPr)$_2$(OtBu)$_2$, M(Et-N—C(H)—N-Et)$_2$(OiPr)$_2$, M(Et-N—C(H)—N-Et)$_2$(OMe)$_2$, M(Et-N—C(H)—N-Et)$_2$(OEt)$_2$, M(Et-N—C(H)—N-Et)$_2$(OnPr)$_2$, M(Et-N—C(H)—N-Et)$_2$(OsBu)$_2$, M(Et-N—C(H)—N-Et)$_2$(OiBu)$_2$, M(Et-N—C(H)—N-Et)$_2$(OtBu)$_2$, M(iPr-N—C(Me)-N-iPr)$_2$(OiPr)$_2$, M(iPr-N—C(Me)-N-iPr)$_2$(OMe)$_2$, M(iPr-N—C(Me)-N-iPr)$_2$(OEt)$_2$, M(iPr-N—C(Me)-N-iPr)$_2$(OnPr)$_2$, M(iPr-N—C(Me)-N-iPr)$_2$(OsBu)$_2$, M(iPr-N—C(Me)-N-iPr)$_2$(OiBu)$_2$, M(iPr-N—C(Me)-N-iPr)$_2$(OtBu)$_2$, M(Et-N—C(Me)-N-Et)$_2$(OiPr)$_2$, M(Et-N—C(Me)-N-Et)$_2$(OMe)$_2$, M(Et-N—C(Me)-N-Et)$_2$(OEt)$_2$, M(Et-N—C(Me)-N-Et)$_2$(OnPr)$_2$, M(Et-N—C(Me)-N-Et)$_2$(OsBu)$_2$, M(Et-N—C(Me)-N-Et)$_2$(OiBu)$_2$, and M(Et-N—C(Me)—N-Et)$_2$(OtBu)$_2$;

the molecule having Formula I, wherein u=1, x=2, y=1, and z=0;
the molecule being selected from the group consisting of M(iPr-N—C(Me)-N-iPr)(OiPr)$_2$(NMe$_2$), M(iPr-N—C(Me)-N-iPr)(OiPr)$_2$(NEt$_2$), M(iPr-N—C(Me)-N-iPr)(OiPr)$_2$(NEtMe), M(Et-N—C(Me)-N-Et)(OiPr)$_2$(NMe$_2$), M(Et-N—C(Me)-N-Et)(OiPr)$_2$(NEt$_2$), M(Et-N—C(Me)-N-Et)(OiPr)$_2$(NEtMe), M(iPr-N—C(NMe$_2$)—N-iPr)(OiPr)$_2$(NMe$_2$), M(iPr-N—C(NMe$_2$)—N-iPr)(OiPr)$_2$(NEt$_2$), and M(iPr-N—C(NMe$_2$)—N-iPr)(OiPr)$_2$(NEtMe), M(iPr-N—C(Me)-N-iPr)(OiPr)$_2$(NMeiPr), M(iPr-N—C(Me)-N-iPr)(OiPr)$_2$(NiPr$_2$), M(iPr-N—C(Me)-N-iPr)(OiPr)$_2$(NMetBu), M(iPr-N—C(Me)-N-iPr)(OiPr)$_2$(NneoPentyl$_2$), M(Et-N—C(Me)-N-Et)(OiPr)$_2$(NMeiPr), M(Et-N—C(Me)-N-Et)(OiPr)$_2$(NiPr$_2$), M(Et-N—C(Me)-N-Et)(OiPr)$_2$(NneoPentyl$_2$), M(iPr-N—C(NMe$_2$)—N-iPr)(OiPr)$_2$(NMeiPr), M(iPr-N—C(NMe$_2$)—N-iPr)(OiPr)$_2$(NiPr$_2$), M(iPr-N—C(NMe$_2$)—N-iPr)(OiPr)$_2$(NneoPentyl$_2$) and M(iPr-N—C(NMe$_2$)—N-iPr)(OiPr)$_2$(NMeiPr);
the molecule having Formula I, wherein u=1, x=2, y=0, and z=1;
the molecule being selected from the group consisting of M(iPr-N—C(Me)-N-iPr)(OiPr)$_2$(O$_2$CMe) and M(Et-N—C(Me)-N-Et)(OiPr)$_2$(O$_2$CMe);
the molecule having Formula II, wherein v=1, x=1, y=0, and z=1;
The molecule being selected from the group consisting of M(iPr-N—(CH$_2$)$_2$—N-iPr)(OiPr)(O$_2$CMe), M(iPr-N—(CH$_2$)$_2$—N-iPr)(OMe)(O$_2$CMe), M(iPr-N—(CH$_2$)$_2$—N-iPr)(OEt)(O$_2$CMe), M(iPr-N—(CH$_2$)$_2$—N-iPr)(OnPr)(O$_2$CMe), M(iPr-N—(CH$_2$)$_2$—N-iPr)(OsBu)(O$_2$CMe), M(iPr-N—(CH$_2$)$_2$—N-iPr)(OiBu)(O$_2$CMe), M(iPr-N—(CH$_2$)$_2$—N-iPr)(OtBu)(O$_2$CMe), M(Et-N—(CH$_2$)$_2$—N-Et)(OiPr)(O$_2$CMe), M(Et-N—(CH$_2$)$_2$—N-Et)(OMe)(O$_2$CMe), M(Et-N—(CH$_2$)$_2$—N-Et)(OEt)(O$_2$CMe), M(Et-N—(CH$_2$)$_2$—N-Et)(OnPr)(O$_2$CMe), M(Et-N—(CH$_2$)$_2$—N-Et)(OsBu)(O$_2$CMe), M(Et-N—(CH$_2$)$_2$—N-Et)(OiBu)(O$_2$CMe), and M(Et-N—(CH$_2$)$_2$—N-Et)(OtBu)(O$_2$CMe);
the molecule having either Formula I or Formula II, wherein u, v, y=0, x=2, and z=2;
the molecule being M(OiPr)$_2$(O$_2$CMe)$_2$;
the molecule having either Formula I or Formula II, wherein u, v, y=0, x=3, and z=1; and
the molecule being M(OiPr)$_3$(O$_2$CMe).

Also disclosed are methods of forming a Hf-containing or Zr-containing layer on a substrate. A reaction chamber is provided having at least one substrate disposed within it. The vapor of at least one of the molecules disclosed above is introduced into the reaction chamber. The vapor is contacted with the substrate to form a Hf-containing or Zr-containing layer on at least one surface of the substrate using a vapor deposition process. The disclosed methods may further include one or more of the following aspects:

NOTATION AND NOMENCLATURE

Certain abbreviations, symbols, and terms are used throughout the following description and claims and include: the abbreviation "PZT" refers to lead zirconium titanates; the abbreviation "R$_1$—NC(R$_3$)N—R$_2$" refers to the following chemical structure:

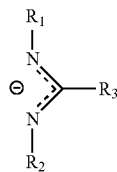

the abbreviation "R$_1$—N(C(R$_3$)$_2$)$_m$—N—R$_2$" refers to the following chemical structure:

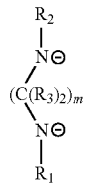

the abbreviation "O$_2$CR$_7$" refers to the following chemical structure:

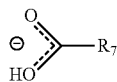

the abbreviation "Cy" refers to cyclohexyl; the abbreviation "Cp" refers to cyclopentadiene; the term "aliphatic group" refers to a C1-C6 linear or branched chain alkyl group; the term "alkyl group" refers to saturated functional groups containing exclusively carbon and hydrogen atoms and includes linear, branched, or cyclic alkyl groups. Examples of linear alkyl groups include without limitation, methyl groups, ethyl groups, n-propyl groups, n-butyl groups, etc. Examples of branched alkyls groups include without limitation, t-butyl. Examples of cyclic alkyl groups include without limitation, cyclopropyl groups, cyclobutyl groups, cyclopentyl groups, cyclohexyl groups, etc. The abbreviation "Me" refers to a methyl group; the abbreviation "Et" refers to an ethyl group; the abbreviation "Pr" refers to a propyl group; the abbreviation "iPr" refers to an isopropyl group; the abbreviation "iBu" refers to an isobutyl group; the abbreviation "nBu" refers to a n-butyl group; the abbreviation "sBu" refers to a sec-butyl group; the abbreviation "tBu" refers to a tertiary butyl group; the abbreviation "N$^Z$-amd" refers to R$_1$—NC(R$_3$) N—R$_2$, wherein R$_3$=a C1-C6 alkyl group and R$_1$ and R$_2$=Z, which is defined as Me, Et, Pr, iPr, nBu, iBu, sBu, or tBu, for example N$^{Me}$-amd is Me-NC(Me)N-Me; the abbreviation "N$^Z$-fmd" refers to R$_1$—NC(R$_3$) N—R$_2$, wherein R$_3$=H and R$_1$ and R$_2$=Z, which is defined as Me, Et, Pr, iPr, or tBu; the abbreviation "N$^Z$-gmd" refers to R$_1$—NC(R$_3$)N—R$_2$ wherein R$_3$=NR$_5$R$_6$ with R$_5$ and R$_6$=H or a C1-C6 alkyl group, and R$_1$ and R$_2$=Z, which is defined as Me, Et, Pr, iPr, nBu, iBu, sBu, or tBu; the abbreviation "THF" refers to tetrahydrofuran; the abbreviation "TMA" refers to trimethyl aluminum; the abbreviation "ALD" refers to atomic layer deposition; the abbreviation "CVD" refers to chemical vapor deposition; the abbreviation "LPCVD" refers to low pressure chemical vapor deposition; the abbreviation "P-CVD" refers to pulsed chemical vapor deposition; the abbreviation "PE-ALD" refers to plasma enhanced atomic layer deposition; the abbreviation "MIM" refers to Metal Insulator Metal (a structure used in capacitors); the abbreviation "DRAM" refers to dynamic random access memory; the abbreviation "FeRAM" refers to ferroelectric random access memory; the abbreviation "CMOS" refers to complementary metal-oxide-semiconductor; the abbreviation "TGA" refers to thermogravimetric analysis.

The standard abbreviations of the elements from the periodic table of elements are used herein. It should be understood that elements may be referred to by these abbreviations (e.g., Hf refers to hafnium, Zr refers to zirconium, etc.).

DESCRIPTION OF PREFERRED EMBODIMENTS

Disclosed are novel hafnium-containing and zirconium-containing precursors, methods of synthesizing the same, and methods of using the same.

The disclosed heteroleptic hafnium-containing and zirconium-containing precursors are derived from different classes of ligand systems, such as amidinate, formamidinate, guanidinate, amide, and/or chelating amide ligands, plus alkoxide ligands. Precursor design may help improve volatility, reduce the melting point (liquids or very low melting solids), increase reactivity with water, and increase thermal stability for wider process window applications.

The disclosed hafnium-containing and zirconium-containing precursors have the following formulae:

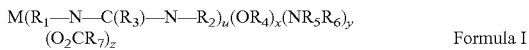    Formula I or

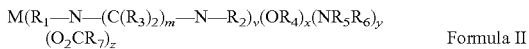    Formula II wherein:
M is Hf or Zr;
$R_1$, $R_2$, $R_5$, $R_6$, and $R_7$ are independently selected from the group consisting of H and C1-C6 alkyl group;
$R_3$=H, C1-C6 alkyl group, or $NMe_2$;
$R_4$ is a C1-C6 alkyl group;
m=2-4;
u=0-2;
v=0-1;
x=1-3;
y=0-2;
z=0-1;
in Formula I, u+x+y+z=4;
in Formula II, 2v+x+y+z=4; and
u, v, or z≥1.

As defined above, the C1-C6 alkyl group includes any linear, branched, or cyclic alkyl groups having from 1 to 6 carbon atoms, including but not limited to Me, tBu, or cyclohexyl groups.

In Formula I, the $R_1$—NC($R_3$)N—$R_2$ ligand has the following chemical structure:

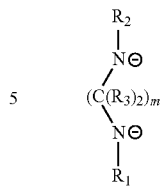

In Formula II, the $R_1$—N—$(C(R_3)_2)_m$—N—$R_2$ ligand has the following chemical structure:

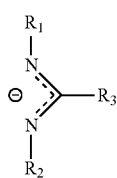

Therefore, although the same elements have been maintained in the backbone of the ligand (i.e., —N—C—N—), the ligand itself has gone from a −1 ligand having one delocalized negative charge between the —N—C—N-backbone to a −2 ligand having a negative charge localized at each nitrogen atom. Additionally, the Formula I ligand has a more rigid structure than the Formula II ligand.

When $R_1$ and $R_3$ are C1-C6 linear or branched alkyl groups in Formula I, $R_1$ and $R_3$ may be independent substituents or they may be linked together to form a monocyclic structure extending from $R_1$ to $R_3$, as demonstrated below.

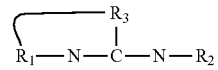

Similarly, when $R_1$, $R_3$ and $R_2$ are C1-C6 linear or branched alkyl groups in Formula I, $R_1$, $R_3$ and $R_2$ may be independent substituents or they may be linked together to form a bicyclic structure, as demonstrated below.

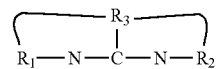

The configuration of the disclosed precursors was selected in order to optimize the reactivity (especially with $H_2O$) and, at the same time, the stability. The M-N bond is weak and will react rapidly on the surface. At the same time, the M-O bond is much stronger and will help stabilize the molecule to avoid fast decomposition. By tuning this molecule, a precursor is obtained that reacts well on the substrate thanks to a weaker site When u=1, x=3, y=0, and z=0 in Formula I, $R_1$ and $R_2$ are preferably Et or iPr, $R_3$ is preferably H, Me, or $NMe_2$, and $R_4$ is preferably a C1-C4 linear or branched alkyl chain. Exemplary precursors include M(iPr-N—C(H)—N-iPr)$_1$(OiPr)$_3$, M(iPr-N—C(H)—N-iPr)$_1$(OMe)$_3$, M(iPr-N—C(H)—N-iPr)$_1$(OEt)$_3$, M(iPr-N—C(H)—N-iPr)$_1$(OnPr)$_3$, M(iPr-N—C(H)—N-iPr)$_1$(OsBu)$_3$, M(iPr-N—C(H)—N-iPr)$_1$(OiBu)$_3$, M(iPr-N—C(H)—N-iPr)$_1$(OtBu)$_3$, M(iPr-N—C(Me)-N-iPr)$_1$(OiPr)$_3$, M(iPr-N—C(Me)-N-iPr)$_1$(OMe)$_3$, M(iPr-N—C(Me)-N-iPr)$_1$(OEt)$_3$, M(iPr-N—C(Me)—N-iPr)$_1$(OnPr)$_3$, M(iPr-N—C(Me)-N-iPr)$_1$(OsBu)$_3$, M(iPr-N—C(Me)-N-iPr)$_1$(OiBu)$_3$, M(iPr-N—C(Me)-N-iPr)$_1$(OtBu)$_3$, M(Et-N—C(Me)-N-Et)$_1$(OEt)$_3$, M(Et-N—C(Me)-N-Et)$_1$(OMe)$_3$, M(Et-N—C(Me)-N-Et)$_1$(OnPr)$_3$, M(Et-N—C(Me)-N-Et)$_1$(OsBu)$_3$, M(Et-N—C(Me)-N-Et)$_1$(OiBu)$_3$, M(Et-N—C(Me)-N-Et)$_1$(OtBu)$_3$, or M(iPr-N—C($NMe_2$)—N-iPr)(OiPr)$_3$.

When M is Hf, the exemplary precursors include Hf(iPr-N—C(H)—N-iPr)$_1$(OiPr)$_3$, Hf(iPr-N—C(H)—N-iPr)$_1$(OMe)$_3$, Hf(iPr-N—C(H)—N-iPr)$_1$(OEt)$_3$, Hf(iPr-N—C(H)—N-iPr)$_1$(OnPr)$_3$, Hf(iPr-N—C(H)—N-iPr)$_1$(OsBu)$_3$, Hf(iPr-N—C(H)—N-iPr)$_1$(OiBu)$_3$, Hf(iPr-N—C(H)—N- iPr)₁(OtBu)₃, Hf(iPr-N—C(Me)-N-iPr)₁(OiPr)₃, Hf(iPr-N—C(Me)-N-iPr)₁(OMe)₃, Hf(iPr-N—C(Me)-N-iPr)₁(OEt)₃, Hf(iPr-N—C(Me)—N-iPr)₁(OnPr)₃, Hf(iPr-N—C(Me)-N-iPr)₁(OsBu)₃, Hf(iPr-N—C(Me)-N-iPr)₁(OiBu)₃, Hf(iPr-N—C(Me)-N-iPr)₁(OtBu)₃, Hf(Et-N—C(Me)-N-Et)₁(OEt)₃, Hf(Et-N—C(Me)-N-Et)₁(OMe)₃, Hf(Et-N—C(Me)-N-Et)₁(OnPr)₃, Hf(Et-N—C(Me)-N-Et)₁(OsBu)₃, Hf(Et-N—C(Me)-N-Et)₁(OiBu)₃, Hf(Et-N—C(Me)-N-Et)₁(OtBu)₃, or Hf(iPr-N—C(NMe₂)—N-iPr)(OiPr)₃.

When M is Zr, the exemplary precursors include Zr(iPr-N—C(H)—N-iPr)₁(OiPr)₃, Zr(iPr-N—C(H)—N-iPr)₁(OMe)₃, Zr(iPr-N—C(H)—N-iPr)₁(OEt)₃, Zr(iPr-N—C(H)—N-iPr)₁(OnPr)₃, Zr(iPr-N—C(H)—N-iPr)₁(OsBu)₃, Zr(iPr-N—C(H)—N-iPr)₁(OiBu)₃, Zr(iPr-N—C(H)—N-iPr)₁(OtBu)₃, Zr(iPr-N—C(Me)-N-iPr)₁(OiPr)₃, Zr(iPr-N—C(Me)-N-iPr)₁(OMe)₃, Zr(iPr-N—C(Me)-N-iPr)₁(OEt)₃, Zr(iPr-N—C(Me)—N-iPr)₁(OnPr)₃, Zr(iPr-N—C(Me)-N-iPr)₁(OsBu)₃, Zr(iPr-N—C(Me)-N-iPr)₁(OiBu)₃, Zr(iPr-N—C(Me)-N-iPr)₁(OtBu)₃, Zr(Et-N—C(Me)-N-Et)₁(OEt)₃, Zr(Et-N—C(Me)-N-Et)₁(OMe)₃, Zr(Et-N—C(Me)-N-Et)₁(OnPr)₃, Zr(Et-N—C(Me)-N-Et)₁(OsBu)₃, Zr(Et-N—C(Me)-N-Et)₁(OiBu)₃, Zr(Et-N—C(Me)-N-Et)₁(OtBu)₃, or Zr(iPr-N—C(NMe₂)—N-iPr)(OiPr)₃.

In this embodiment, the preferred exemplary precursors are Hf(iPr-N—C(Me)-N-iPr)₁(OiPr)₃ or Zr(iPr-N—C(Me)-N-iPr)₁(OiPr)₃.

When m=2 or 3, v=1, x=2, y=0, and z=0 in Formula II, $R_1$ and $R_2$ are preferably Et or iPr, $R_3$ is preferably H, and $R_4$ is preferably a C1-C4 linear or branched alkyl chain. More preferably, $R_1$ and $R_2$ are not Me when m=2. Exemplary precursors include M(iPr-N—(CH₂)₂—N-iPr)₁(OiPr)₂, M(iPr-N—(CH₂)₂—N-iPr)₁(OMe)₂, M(iPr-N—(CH₂)₂—N-iPr)₁(OEt)₂, M(iPr-N—(CH₂)₂—N-iPr)₁(OnPr)₂, M(iPr-N—(CH₂)₂—N-iPr)₁(OsBu)₂, M(iPr-N—(CH₂)₂—N-iPr)₁(OiBu)₂, M(iPr-N—(CH₂)₂—N-iPr)₁(OtBu)₂, M(Et-N—(CH₂)₂—N-Et)₁(OiPr)₂, M(Et-N—(CH₂)₂—N-Et)₁(OMe)₂, M(Et-N—(CH₂)₂—N-Et)₁(OEt)₂, M(Et-N—(CH₂)₂—N-Et)₁(OnPr)₂, M(Et-N—(CH₂)₂—N-Et)₁(OsBu)₂, M(Et-N—(CH₂)₂—N-Et)₁(OiBu)₂, M(Et-N—(CH₂)₂—N-Et)₁(OtBu)₂, M(iPr-N—(CH₂)₃—N-iPr)₁(OiPr)₂, M(iPr-N—(CH₂)₃—N-iPr)₁(OMe)₂, M(iPr-N—(CH₂)₃—N-iPr)₁(OEt)₂, M(iPr-N—(CH₂)₃—N-iPr)₁(OnPr)₂, M(iPr-N—(CH₂)₃—N-iPr)₁(OsBu)₂, M(iPr-N—(CH₂)₃—N-iPr)₁(OiBu)₂, M(iPr-N—(CH₂)₃—N-iPr)₁(OtBu)₂, M(Et-N—(CH₂)₃—N-Et)₁(OiPr)₂, M(Et-N—(CH₂)₃—N-Et)₁(OMe)₂, M(Et-N—(CH₂)₃—N-Et)₁(OEt)₂, M(Et-N—(CH₂)₃—N-Et)₁(OnPr)₂, M(Et-N—(CH₂)₃—N-Et)₁(OsBu)₂, M(Et-N—(CH₂)₃—N-Et)₁(OiBu)₂, or M(Et-N—(CH₂)₃—N-Et)₁(OtBu)₂.

When M is Hf, the exemplary precursors include Hf(iPr-N—(CH₂)₂—N-iPr)₁(OiPr)₂, Hf(iPr-N—(CH₂)₂—N-iPr)₁(OMe)₂, Hf(iPr-N—(CH₂)₂—N-iPr)₁(OEt)₂, Hf(iPr-N—(CH₂)₂—N-iPr)₁(OnPr)₂, Hf(iPr-N—(CH₂)₂—N-iPr)₁(OsBu)₂, Hf(iPr-N—(CH₂)₂—N-iPr)₁(OiBu)₂, Hf(iPr-N—(CH₂)₂—N-iPr)₁(OtBu)₂, Hf(Et-N—(CH₂)₂—N-Et)₁(OiPr)₂, Hf(Et-N—(CH₂)₂—N-Et)₁(OMe)₂, Hf(Et-N—(CH₂)₂—N-Et)₁(OEt)₂, Hf(Et-N—(CH₂)₂—N-Et)₁(OnPr)₂, Hf(Et-N—(CH₂)₂—N-Et)₁(OsBu)₂, Hf(Et-N—(CH₂)₂—N-Et)₁(OiBu)₂, Hf(Et-N—(CH₂)₂—N-Et)₁(OtBu)₂, Hf(iPr-N—(CH₂)₃—N-iPr)₁(OiPr)₂, Hf(iPr-N—(CH₂)₃—N-iPr)₁(OMe)₂, Hf(iPr-N—(CH₂)₃—N-iPr)₁(OEt)₂, Hf(iPr-N—(CH₂)₃—N-iPr)₁(OnPr)₂, Hf(iPr-N—(CH₂)₃—N-iPr)₁(OsBu)₂, Hf(iPr-N—(CH₂)₃—N-iPr)₁(OiBu)₂, Hf(iPr-N—(CH₂)₃—N-iPr)₁(OtBu)₂, Hf(Et-N—(CH₂)₃—N-Et)₁(OiPr)₂, Hf(Et-N—(CH₂)₃—N-Et)₁(OMe)₂, Hf(Et-N—(CH₂)₃—N-Et)₁(OEt)₂, Hf(Et-N—(CH₂)₃—N-Et)₁(OnPr)₂, Hf(Et-N—(CH₂)₃—N-Et)₁(OsBu)₂, Hf(Et-N—(CH₂)₃—N-Et)₁(OiBu)₂, Hf(Et-N—(CH₂)₃—N-Et)₁(OtBu)₂, or Hf(Et-N—(CH₂)₃—N-Et)₁(OtBu)₂.

When M is Zr, the exemplary precursors include Zr(iPr-N—(CH₂)₂—N-iPr)₁(OiPr)₂, Zr(iPr-N—(CH₂)₂—N-iPr)₁(OMe)₂, Zr(iPr-N—(CH₂)₂—N-iPr)₁(OEt)₂, Zr(iPr-N—(CH₂)₂—N-iPr)₁(OnPr)₂, Zr(iPr-N—(CH₂)₂—N-iPr)₁(OsBu)₂, Zr(iPr-N—(CH₂)₂—N-iPr)₁(OiBu)₂, Zr(iPr-N—(CH₂)₂—N-iPr)₁(OtBu)₂, Zr(Et-N—(CH₂)₂—N-Et)₁(OiPr)₂, Zr(Et-N—(CH₂)₂—N-Et)₁(OMe)₂, Zr(Et-N—(CH₂)₂—N-Et)₁(OEt)₂, Zr(Et-N—(CH₂)₂—N-Et)₁(OnPr)₂, Zr(Et-N—(CH₂)₂—N-Et)₁(OsBu)₂, Zr(Et-N—(CH₂)₂—N-Et)₁(OiBu)₂, Zr(Et-N—(CH₂)₂—N-Et)₁(OtBu)₂, Zr(iPr-N—(CH₂)₃—N-iPr)₁(OiPr)₂, Zr(iPr-N—(CH₂)₃—N-iPr)₁(OMe)₂, Zr(iPr-N—(CH₂)₃—N-iPr)₁(OEt)₂, Zr(iPr-N—(CH₂)₃—N-iPr)₁(OnPr)₂, Zr(iPr-N—(CH₂)₃—N-iPr)₁(OsBu)₂, Zr(iPr-N—(CH₂)₃—N-iPr)₁(OiBu)₂, Zr(iPr-N—(CH₂)₃—N-iPr)₁(OtBu)₂, Zr(Et-N—(CH₂)₃—N-Et)₁(OiPr)₂, Zr(Et-N—(CH₂)₃—N-Et)₁(OMe)₂, Zr(Et-N—(CH₂)₃—N-Et)₁(OEt)₂, Zr(Et-N—(CH₂)₃—N-Et)₁(OnPr)₂, Zr(Et-N—(CH₂)₃—N-Et)₁(OsBu)₂, Zr(Et-N—(CH₂)₃—N-Et)₁(OiBu)₂, or Zr(Et-N—(CH₂)₃—N-Et)₁(OtBu)₂.

In this embodiment, the preferred exemplary precursors are Hf(iPr-N—(CH₂)₂—N-iPr)₁(OiPr)₂, Hf(Et-N—(CH₂)₂—N-Et)₁(OiPr)₂, Hf(Et-N—(CH₂)₂—N-Et)₁(OiPr)₂, Zr(iPr-N—(CH₂)₂—N-iPr)₁(OiPr)₂, Zr(Et-N—(CH₂)₃—N-Et)₁(OiPr)₂, or Zr(Et-N—(CH₂)₂—N-Et)₁(OiPr)₂.

When u=2, x=2, y=0, and z=0 in Formula I, the precursor has the following chemical structure:

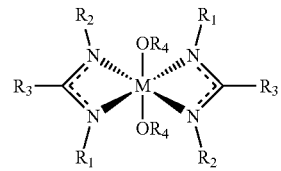

In this embodiment, $R_1$ and $R_2$ are preferably Et or iPr, $R_3$ is preferably H or Me, and $R_4$ is preferably a C1-C4 linear or branched alkyl chain. More preferably, $R_3$ is not NMe₂. Exemplary precursors include M(iPr-N—C(H)—N-iPr)₂(OiPr)₂, M(iPr-N—C(H)—N-iPr)₂(OMe)₂, M(iPr-N—C(H)—N-iPr)₂(OEt)₂, M(iPr-N—C(H)—N-iPr)₂(OnPr)₂, M(iPr-N—C(H)—N-iPr)₂(OsBu)₂, M(iPr-N—C(H)—N-iPr)₂(OiBu)₂, M(iPr-N—C(H)—N-iPr)₂(OtBu)₂, M(Et-N—C(H)—N-Et)₂(OiPr)₂, M(Et-N—C(H)—N-Et)₂(OMe)₂, M(Et-N—C(H)—N-Et)₂(OEt)₂, M(Et-N—C(H)—N-Et)₂(OnPr)₂, M(Et-N—C(H)—N-Et)₂(OsBu)₂, M(Et-N—C(H)—N-Et)₂(OiBu)₂, M(Et-N—C(H)—N-Et)₂(OtBu)₂, M(iPr-N—C(Me)-N-iPr)₂(OiPr)₂, M(iPr-N—C(Me)-N-iPr)₂(OMe)₂, M(iPr-N—C(Me)-N-iPr)₂(OEt)₂, M(iPr-N—C(Me)-N-iPr)₂(OnPr)₂, M(iPr-N—C(Me)—N-iPr)₂(OsBu)₂, M(iPr-N—C(Me)-N-iPr)₂(OiBu)₂, M(iPr-N—C(Me)-N-iPr)₂(OtBu)₂, M(Et-N—C(Me)-N-Et)₂(OiPr)₂, M(Et-N—C(Me)-N-Et)₂(OMe)₂, M(Et-N—C(Me)-N-Et)₂(OEt)₂, M(Et-N—C(Me)-N-Et)₂(OnPr)₂, M(Et-N—C(Me)-N-Et)₂(OsBu)₂, M(Et-N—C(Me)-N-Et)₂(OiBu)₂, and M(Et-N—C(Me)-N-Et)₂(OtBu)₂.

When M is Hf, the exemplary precursors include Hf(iPr-N—C(H)—N-iPr)₂(OiPr)₂, Hf(iPr-N—C(H)—N-iPr)₂(OMe)₂, Hf(iPr-N—C(H)—N-iPr)₂(OEt)₂, Hf(iPr-N—C(H)—N-iPr)₂(OnPr)₂, Hf(iPr-N—C(H)—N-iPr)₂(OsBu)₂, Hf(iPr-N—C(H)—N-iPr)₂(OiBu)₂, Hf(iPr-N—C(H)—N-iPr)₂(OtBu)₂, Hf(Et-N—C(H)—N-Et)₂(OiPr)₂, Hf(Et-N—C(H)—N-Et)₂(OMe)₂, Hf(Et-N—C(H)—N-Et)₂(OEt)₂, Hf(Et-N—C(H)—N-Et)₂(OnPr)₂, Hf(Et-N—C(H)—N-Et)₂(OsBu)₂, Hf(Et-N—C(H)—N-Et)₂(OiBu)₂, Hf(Et-N—C(H)—N-Et)₂(OtBu)₂, Hf(iPr-N—C(Me)-N-iPr)₂(OiPr)₂, Hf(iPr-N=C(Me)-N-iPr)₂(OMe)₂, Hf(iPr-N=C(Me)-N-iPr)₂(OEt)₂, Hf(iPr-N=C(Me)-N-iPr)₂(OnPr)₂, Hf(iPr-N=C(Me)-N-iPr)₂(OsBu)₂, Hf(iPr-N=C(Me)-N-iPr)₂(OiBu)₂, Hf(iPr-N=C(Me)-N-iPr)₂(OtBu)₂, Hf(Et-N=C(Me)-N-Et)₂(OiPr)₂, Hf(Et-N=C(Me)-N-Et)₂(OMe)₂, Hf(Et-N=C(Me)-N-Et)₂(OEt)₂, Hf(Et-N=C(Me)-N-Et)₂(OnPr)₂, Hf(Et-N=C(Me)-N-Et)₂(OsBu)₂, Hf(Et-N=C(Me)-N-Et)₂(OiBu)₂, and Hf(Et-N=C(Me)-N-Et)₂(OtBu)₂.

When M is Zr, the exemplary precursors include Zr(iPr-N=C(H)-N-iPr)₂(OiPr)₂, Zr(iPr-N=C(H)-N-iPr)₂(OMe)₂, Zr(iPr-N=C(H)-N-iPr)₂(OEt)₂, Zr(iPr-N=C(H)-N-iPr)₂(OnPr)₂, Zr(iPr-N=C(H)-N-iPr)₂(OsBu)₂, Zr(iPr-N=C(H)-N-iPr)₂(OiBu)₂, Zr(iPr-N=C(H)-N-iPr)₂(OtBu)₂, Zr(Et-N=C(H)-N-Et)₂(OiPr)₂, Zr(Et-N=C(H)-N-Et)₂(OMe)₂, Zr(Et-N=C(H)-N-Et)₂(OEt)₂, Zr(Et-N=C(H)-N-Et)₂(OnPr)₂, Zr(Et-N=C(H)-N-Et)₂(OsBu)₂, Zr(Et-N=C(H)-N-Et)₂(OiBu)₂, Zr(Et-N=C(H)-N-Et)₂(OtBu)₂, Zr(iPr-N=C(Me)-N-iPr)₂(OiPr)₂, Zr(iPr-N=C(Me)-N-iPr)₂(OMe)₂, Zr(iPr-N=C(Me)-N-iPr)₂(OEt)₂, Zr(iPr-N=C(Me)-N-iPr)₂(OnPr)₂, Zr(iPr-N=C(Me)-N-iPr)₂(OsBu)₂, Zr(iPr-N=C(Me)-N-iPr)₂(OiBu)₂, Zr(iPr-N=C(Me)-N-iPr)₂(OtBu)₂, Zr(Et-N=C(Me)-N-Et)₂(OiPr)₂, Zr(Et-N=C(Me)-N-Et)₂(OMe)₂, Zr(Et-N=C(Me)-N-Et)₂(OEt)₂, Zr(Et-N=C(Me)-N-Et)₂(OnPr)₂, Zr(Et-N=C(Me)-N-Et)₂(OsBu)₂, Zr(Et-N=C(Me)-N-Et)₂(OiBu)₂, and Zr(Et-N=C(Me)-N-Et)₂(OtBu)₂.

In this embodiment, the preferred exemplary precursor is Hf(iPr-N=C(H)-N-iPr)₂(OiPr)₂, Hf(iPr-N=C(Me)-N-iPr)₂(OiPr)₂, Zr(iPr-N=C(H)-N-iPr)₂(OiPr)₂, or Zr(iPr-N=C(Me)-N-iPr)₂(OiPr)₂.

When u=1, x=2, y=1, and z=0 in Formula I, the precursor has the following chemical structure:

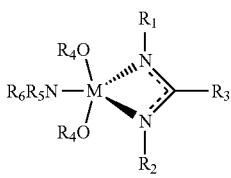

In this embodiment, $R_1$ and $R_2$ are preferably Et or iPr; $R_3$ is preferably H, Me, or $NMe_2$; $R_4$ is preferably iPr; and $R_5$ and $R_6$ preferably are independently Me or Et. Exemplary precursors include M(iPr-N=C(Me)-N-iPr)(OiPr)₂(NMe₂), M(iPr-N=C(Me)-N-iPr)(OiPr)₂(NEt₂), M(iPr-N=C(Me)-N-iPr)(OiPr)₂(NEtMe), M(Et-N=C(Me)-N-Et)(OiPr)₂(NMe₂), M(Et-N=C(Me)-N-Et)(OiPr)₂(NEt₂), M(Et-N=C(Me)-N-Et)(OiPr)₂(NEtMe), M(iPr-N=C(NMe₂)-N-iPr)(OiPr)₂(NMe₂), M(iPr-N=C(NMe₂)-N-iPr)(OiPr)₂(NEt₂), M(iPr-N=C(NMe₂)-N-iPr)(OiPr)₂(NEtMe), M(iPr-N=C(Me)-N-iPr)(OiPr)₂(NMeiPr), M(iPr-N=C(Me)-N-iPr)(OiPr)₂(NiPr₂), M(iPr-N=C(Me)-N-iPr)(OiPr)₂(NMetBu), M(iPr-N=C(Me)-N-iPr)(OiPr)₂(NneoPentyl₂), M(Et-N=C(Me)-N-Et)(OiPr)₂(NMeiPr), M(Et-N=C(Me)-N-Et)(OiPr)₂(NiPr₂), M(Et-N=C(Me)-N-Et)(OiPr)₂(NneoPentyl₂), M(iPr-N=C(NMe₂)-N-iPr)(OiPr)₂(NMeiPr), M(iPr-N=C(NMe₂)-N-iPr)(OiPr)₂(NiPr₂), M(iPr-N=C(NMe₂)-N-iPr)(OiPr)₂(NneoPentyl₂) and M(iPr-N=C(NMe₂)-N-iPr)(OiPr)₂(NMeiPr).

When M is Hf, the exemplary precursors include Hf(iPr-N=C(Me)-N-iPr)(OiPr)₂(NMe₂), Hf(iPr-N=C(Me)-N-iPr)(OiPr)₂(NEt₂), Hf(iPr-N=C(Me)-N-iPr)(OiPr)₂(NEtMe), Hf(Et-N=C(Me)-N-Et)(OiPr)₂(NMe₂), Hf(Et-N=C(Me)-N-Et)(OiPr)₂(NEt₂), Hf(Et-N=C(Me)-N-Et)(OiPr)₂(NEtMe), Hf(iPr-N=C(NMe₂)-N-iPr)(OiPr)₂(NMe₂), Hf(iPr-N=C(NMe₂)-N-iPr)(OiPr)₂(NEt₂), Hf(iPr-N=C(NMe₂)-N-iPr)(OiPr)₂(NEtMe), Hf(iPr-N=C(Me)-N-iPr)(OiPr)₂(NMeiPr), Hf(iPr-N=C(Me)-N-iPr)(OiPr)₂(NiPr₂), Hf(iPr-N=C(Me)-N-iPr)(OiPr)₂(NMetBu), Hf(iPr-N=C(Me)-N-iPr)(OiPr)₂(NneoPentyl₂), Hf(Et-N=C(Me)-N-Et)(OiPr)₂(NMeiPr), Hf(Et-N=C(Me)-N-Et)(OiPr)₂(NiPr₂), Hf(Et-N=C(Me)-N-Et)(OiPr)₂(NneoPentyl₂), Hf(iPr-N=C(NMe₂)-N-iPr)(OiPr)₂(NMeiPr), Hf(iPr-N=C(NMe₂)-N-iPr)(OiPr)₂(NiPr₂), Hf(iPr-N=C(NMe₂)-N-iPr)₂(NneoPentyl₂) and Hf(iPr-N=C(NMe₂)-N-iPr)(OiPr)₂(NMeiPr).

When M is Zr, the exemplary precursors include Zr(iPr-N=C(Me)-N-iPr)(OiPr)₂(NMe₂), Zr(iPr-N=C(Me)-N-iPr)(OiPr)₂(NEt₂), Zr(iPr-N=C(Me)-N-iPr)(OiPr)₂(NEtMe), Zr(Et-N=C(Me)-N-Et)(OiPr)₂(NMe₂), Zr(Et-N=C(Me)-N-Et)(OiPr)₂(NEt₂), Zr(Et-N=C(Me)-N-Et)(OiPr)₂(NEtMe), Zr(iPr-N=C(NMe₂)-N-iPr)(OiPr)₂(NMe₂), Zr(iPr-N=C(NMe₂)-N-iPr)(OiPr)₂(NEt₂), Zr(iPr-N=C(NMe₂)-N-iPr)(OiPr)₂(NEtMe), Zr(iPr-N=C(Me)-N-iPr)(OiPr)₂(NMeiPr), Zr(iPr-N=C(Me)-N-iPr)(OiPr)₂(NiPr₂), Zr(iPr-N=C(Me)-N-iPr)(OiPr)₂(NMetBu), Zr(iPr-N=C(Me)-N-iPr)(OiPr)₂(NneoPentyl₂), Zr(Et-N=C(Me)-N-Et)(OiPr)₂(NMeiPr), Zr(Et-N=C(Me)-N-Et)(OiPr)₂(NiPr₂), Zr(Et-N=C(Me)-N-Et)(OiPr)₂(NneoPentyl₂), Zr(iPr-N=C(NMe₂)-N-iPr)(OiPr)₂(NMeiPr), Zr(iPr-N=C(NMe₂)-N-iPr)(OiPr)₂(NiPr₂), Zr(iPr-N=C(NMe₂)-N-iPr)(OiPr)₂(NneoPentyl₂), and Zr(iPr-N=C(NMe₂)-N-iPr)(OiPr)₂(NMeiPr).

In this embodiment, the preferred exemplary precursor is Hf(iPr-N=C(Me)-N-iPr)(OiPr)₂(NMe₂) or Zr(iPr-N=C(Me)-N-iPr)(OiPr)₂(NMe₂).

When u=1, x=2, y=0, and z=1 in Formula I, the precursor has the following chemical structure:

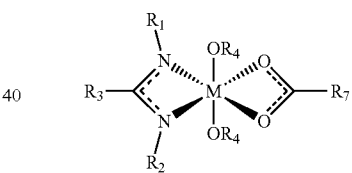

In this embodiment, $R_1$ and $R_2$ are preferably Et or iPr; $R_3$ is preferably H or Me; $R_4$ is preferably iPr; and $R_7$ is preferably Me. Exemplary precursors include M(iPr-N=C(Me)-N-iPr)(OiPr)₂(O₂CMe) and M(Et-N=C(Me)-N-Et)(OiPr)₂(O₂CMe). When M is Hf, the exemplary precursors include Hf(iPr-N=C(Me)-N-iPr)(OiPr)₂(O₂CMe) and Hf(Et-N=C(Me)-N-Et)(OiPr)₂(O₂CMe). When M is Zr, the exemplary precursors include Zr(iPr-N=C(Me)-N-iPr)(OiPr)₂(O₂CMe) and Zr(Et-N=C(Me)-N-Et)(OiPr)₂(O₂CMe).

When v=1, x=1, y=0, and z=1 in Formula II, the precursor has the following chemical structure:

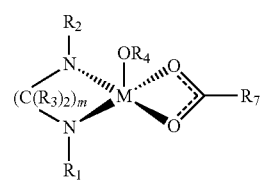

When m=2, v=1, x=1, y=0, z=1, and $R_3$=H, the precursor has the following chemical structure:

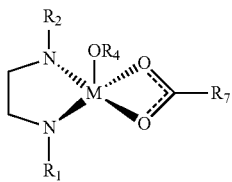

When m=3, v=1, x=1, y=0, z=1, and $R_3$=H, the precursor has the following chemical structure:

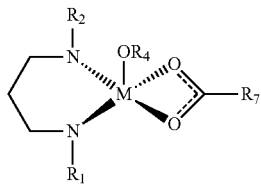

In these embodiments, m is preferably 2 or 3, $R_1$ and $R_2$ are preferably Et or iPr; $R_3$ is preferably H; $R_4$ is preferably a C1-C4 linear or branched alkyl chain; and $R_7$ is preferably Me. Exemplary precursors include M(iPr-N—(CH$_2$)$_2$—N-iPr)(OiPr)(O$_2$CMe), M(iPr-N—(CH$_2$)$_2$—N-iPr)(OMe)(O$_2$CMe), M(iPr-N—(CH$_2$)$_2$—N-iPr)(OEt)(O$_2$CMe), M(iPr-N—(CH$_2$)$_2$—N-iPr)(OnPr)(O$_2$CMe), M(iPr-N—(CH$_2$)$_2$—N-iPr)(OsBu)(O$_2$CMe), M(iPr-N—(CH$_2$)$_2$—N-iPr)(OiBu)(O$_2$CMe), M(iPr-N—(CH$_2$)$_2$—N-iPr)(OtBu)(O$_2$CMe), M(Et-N—(CH$_2$)$_2$—N-Et)(OiPr)(O$_2$CMe), M(Et-N—(CH$_2$)$_2$—N-Et)(OMe)(O$_2$CMe), M(Et-N—(CH$_2$)$_2$—N-Et)(OEt)(O$_2$CMe), M(Et-N—(CH$_2$)$_2$—N-Et)(OnPr)(O$_2$CMe), M(Et-N—(CH$_2$)$_2$—N-Et)(OsBu)(O$_2$CMe), M(Et-N—(CH$_2$)$_2$—N-Et)(OiBu)(O$_2$CMe), and M(Et-N—(CH$_2$)$_2$—N-Et)(OtBu)(O$_2$CMe).

When M is Hf, the exemplary precursors include Hf(iPr-N—(CH$_2$)$_2$—N-iPr)(OiPr)(O$_2$CMe), Hf(iPr-N—(CH$_2$)$_2$—N-iPr)(OMe)(O$_2$CMe), Hf(iPr-N—(CH$_2$)$_2$—N-iPr)(OEt)(O$_2$CMe), Hf(iPr-N—(CH$_2$)$_2$—N-iPr)(OnPr)(O$_2$CMe), Hf(iPr-N—(CH$_2$)$_2$—N-iPr)(OsBu)(O$_2$CMe), Hf(iPr-N—(CH$_2$)$_2$—N-iPr)(OiBu)(O$_2$CMe), Hf(iPr-N—(CH$_2$)$_2$—N-iPr)(OtBu)(O$_2$CMe), Hf(Et-N—(CH$_2$)$_2$—N-Et)(OiPr)(O$_2$CMe), Hf(Et-N—(CH$_2$)$_2$—N-Et)(OMe)(O$_2$CMe), Hf(Et-N—(CH$_2$)$_2$—N-Et)(OEt)(O$_2$CMe), Hf(Et-N—(CH$_2$)$_2$—N-Et)(OnPr)(O$_2$CMe), Hf(Et-N—(CH$_2$)$_2$—N-Et)(OsBu)(O$_2$CMe), Hf(Et-N—(CH$_2$)$_2$—N-Et)(OiBu)(O$_2$CMe), and Hf(Et-N—(CH$_2$)$_2$—N-Et)(OtBu)(O$_2$CMe).

When M is Zr, the exemplary precursors include Zr(iPr-N—(CH$_2$)$_2$—N-iPr)(OiPr)(O$_2$CMe), Zr(iPr-N—(CH$_2$)$_2$—N-iPr)(OMe)(O$_2$CMe), Zr(iPr-N—(CH$_2$)$_2$—N-iPr)(OEt)(O$_2$CMe), Zr(iPr-N—(CH$_2$)$_2$—N-iPr)(OnPr)(O$_2$CMe), Zr(iPr-N—(CH$_2$)$_2$—N-iPr)(OsBu)(O$_2$CMe), Zr(iPr-N—(CH$_2$)$_2$—N-iPr)(OiBu)(O$_2$CMe), Zr(iPr-N—(CH$_2$)$_2$—N-iPr)(OtBu)(O$_2$CMe), Zr(Et-N—(CH$_2$)$_2$—N-Et)(OiPr)(O$_2$CMe), Zr(Et-N—(CH$_2$)$_2$—N-Et)(OMe)(O$_2$CMe), Zr(Et-N—(CH$_2$)$_2$—N-Et)(OEt)(O$_2$CMe), Zr(Et-N—(CH$_2$)$_2$—N-Et)(OnPr)(O$_2$CMe), Zr(Et-N—(CH$_2$)$_2$—N-Et)(OsBu)(O$_2$CMe), Zr(Et-N—(CH$_2$)$_2$—N-Et)(OiBu)(O$_2$CMe), and Zr(Et-N—(CH$_2$)$_2$—N-Et)(OtBu)(O$_2$CMe).

When u=1, x=1, y=2, and z=0 in Formula I, exemplary precursors include M(iPr-N—C(Me)-N-iPr)(OiPr) (NMe$_2$)$_2$, M(iPr-N—C(Me)-N-iPr)(OiPr)(NEt$_2$)$_2$, M(iPr-N—C(Me)-N-iPr)(OiPr)(NEtMe)$_2$, M(Et-N—C(Me)-N-Et)(OiPr)(NMe$_2$)$_2$, M(Et-N—C(Me)-N-Et)(OiPr)(NEt$_2$)$_2$, M(Et-N—C(Me)-N-Et)(OiPr)(NEtMe)$_2$, M(iPr-N—C(NMe$_2$)—N-iPr)(OiPr)(NMe$_2$)$_2$, M(iPr-N—C(NMe$_2$)—N-iPr)(OiPr)(NEt$_2$)$_2$, and M(iPr-N—C(NMe$_2$)—N-iPr)(OiPr)(NEtMe)$_2$.

When M is Hf, the exemplary precursors include Hf(iPr-N—C(Me)-N-iPr)(OiPr) (NMe$_2$)$_2$, Hf(iPr-N—C(Me)-N-iPr)(OiPr)(NEt$_2$)$_2$, Hf(iPr-N—C(Me)-N-iPr)(OiPr)(NEtMe)$_2$, Hf(Et-N—C(Me)-N-Et)(OiPr)(NMe$_2$)$_2$, Hf(Et-N—C(Me)-N-Et)(OiPr)(NEt$_2$)$_2$, Hf(Et-N—C(Me)-N-Et)(OiPr)(NEtMe)$_2$, Hf(iPr-N—C(NMe$_2$)—N-iPr)(OiPr)(NMe$_2$)$_2$, Hf(iPr-N—C(NMe$_2$)—N-iPr)(OiPr)(NEt$_2$)$_2$, and Hf(iPr-N—C(NMe$_2$)—N-iPr)(OiPr)(NEtMe)$_2$.

When M is Zr, the exemplary precursors include Zr(iPr-N—C(Me)-N-iPr)(OiPr) (NMe$_2$)$_2$, Zr(iPr-N—C(Me)-N-iPr)(OiPr)(NEt$_2$)$_2$, Zr(iPr-N—C(Me)-N-iPr)(OiPr)(NEtMe)$_2$, Zr(Et-N—C(Me)-N-Et)(OiPr)(NMe$_2$)$_2$, Zr(Et-N—C(Me)-N-Et)(OiPr)(NEt$_2$)$_2$, Zr(Et-N—C(Me)-N-Et)(OiPr)(NEtMe)$_2$, Zr(iPr-N—C(NMe$_2$)—N-iPr)(OiPr)(NMe$_2$)$_2$, Zr(iPr-N—C(NMe$_2$)—N-iPr)(OiPr)(NEt$_2$)$_2$, and Zr(iPr-N—C(NMe$_2$)—N-iPr)(OiPr)(NEtMe)$_2$ When v=1, x=1, y=1, and z=0 in Formula II, exemplary precursors include M(iPr-N—(CH$_2$)$_2$—N-iPr)(OiPr)(NMe$_2$), M(iPr-N—(CH$_2$)$_2$—N-iPr)(OiPr)(NEt$_2$), M(iPr-N—(CH$_2$)$_2$—N-iPr)(OiPr)(NEtMe), M(Et-N—(CH$_2$)$_2$—N-Et)(OiPr)(NMe$_2$), M(Et-N—(CH$_2$)$_2$—N-Et)(OiPr)(NEt$_2$), and M(Et-N—(CH$_2$)$_2$—N-Et)(OiPr)(NEtMe). When M is Hf, the exemplary precursors include Hf(iPr-N—(CH$_2$)$_2$—N-iPr)(OiPr)(NMe$_2$), Hf(iPr-N—(CH$_2$)$_2$—N-iPr)(OiPr)(NEt$_2$), Hf(iPr-N—(CH$_2$)$_2$—N-iPr)(OiPr)(NEtMe), Hf(Et-N—(CH$_2$)$_2$—N-Et)(OiPr)(NMe$_2$), Hf(Et-N—(CH$_2$)$_2$—N-Et)(OiPr)(NEt$_2$), and Hf(Et-N—(CH$_2$)$_2$—N-Et)(OiPr)(NEtMe). When M is Zr, the exemplary precursors include Zr(iPr-N—(CH$_2$)$_2$—N-iPr)(OiPr)(NMe$_2$), Zr(iPr-N—(CH$_2$)$_2$—N-iPr)(OiPr)(NEt$_2$), Zr(iPr-N—(CH$_2$)$_2$—N-iPr)(OiPr)(NEtMe), Zr(Et-N—(CH$_2$)$_2$—N-Et)(OiPr)(NMe$_2$), Zr(Et-N—(CH$_2$)$_2$—N-Et)(OiPr)(NEt$_2$), and Zr(Et-N—(CH$_2$)$_2$—N-Et)(OiPr)(NEtMe).

When u=1, x=1, y=0, and z=2 in Formula I, exemplary precursors include M(iPr-N—C(Me)-N-iPr)(OiPr)(O$_2$CMe)$_2$ and M(Et-N—C(Me)-N-Et)(OiPr)(O$_2$CMe)$_2$. When M is Hf, the exemplary precursors include Hf(iPr-N—C(Me)-N-iPr)(OiPr) (O$_2$CMe)$_2$ and Hf(Et-N—C(Me)-N-Et)(OiPr)(O$_2$CMe)$_2$. When M is Zr, the exemplary precursors include Zr(iPr-N—C(Me)-N-iPr)(OiPr) (O$_2$CMe)$_2$ and Zr(Et-N—C(Me)-N-Et)(OiPr)(O$_2$CMe)$_2$.

When u, v, y=0, x=2, and z=2 in either of Formula I or Formula II, exemplary precursors include M(OiPr)$_2$(O$_2$CMe)$_2$, or Hf(OiPr)$_2$(O$_2$CMe)$_2$ when M is Hf and Zr(OiPr)$_2$(O$_2$CMe)$_2$ when M is Zr.

When u, v, y=0, x=3, and z=1 in either of Formula I or Formula II, exemplary precursors include M(OiPr)$_3$(O$_2$CMe), or Hf(OiPr)$_3$(O$_2$CMe) when M is Hf and Zr(OiPr)$_3$(O$_2$CMe) when M is Zr.

The disclosed precursors may be synthesized by combining a hydrocarbon solution of H(R$_1$—N—C(R$_3$)—N—R$_2$) with a neat or hydrocarbon solution of a hafnium or zirconium compound, such as Hf(OR$_4$)$_3$(NR$_5$R$_6$), Hf(OR$_4$)$_2$(NR$_5$R$_6$)$_2$, Zr(OR$_4$)$_3$(NR$_5$R$_6$), or Zr(OR$_4$)$_2$(NR$_5$R$_6$)$_2$, under atmosphere of nitrogen, the outlet of the mixing flask being connected to an oil bubbler. Exemplary hydrocarbon solutions include pentane. The resulting solution is stirred at room temperature overnight. Where applicable, HO$_2$CR$_7$ may be added and further stirred for 6-12 hours. Solvent and volatiles are removed from the reaction mixture under vacuum. Purification of the resulting liquid or solid is carried out by distillation or sublimation, respectively. Additional synthesis details are provided in the Examples.

Also disclosed are methods of using the disclosed hafnium-containing and zirconium-containing precursors for vapor deposition methods. The disclosed methods provide for the use of the hafnium-containing and zirconium-containing precursors for deposition of hafnium-containing and zirconium-containing films, respectively. The disclosed methods may be useful in the manufacture of semiconductor, photovoltaic, LCD-TFT, or flat panel type devices. The method includes: providing a substrate; providing a vapor including at least one of the disclosed hafnium-containing or zirconium-containing precursors: and contacting the vapor with the substrate (and typically directing the vapor to the substrate) to form a hafnium-containing or zirconium-containing layer on at least one surface of the substrate.

The disclosed methods also provide for forming a bimetal-containing layer on a substrate using a vapor deposition process. The disclosed methods may be useful in the manufacture of semiconductor, photovoltaic, LCD-TFT, or flat panel type devices. The method includes: providing a substrate; providing a vapor including at least one of the disclosed hafnium-containing or zirconium-containing precursors and contacting the vapor with the substrate (and typically directing the vapor to the substrate) to form a bi metal-containing layer on at least one surface of the substrate. An oxygen source, such as $O_3$, $O_2$, $H_2O$, and NO, preferably $H_2O$, may also be provided.

The disclosed hafnium-containing and zirconium-containing precursors may be used to deposit hafnium-containing and zirconium-containing films using any deposition methods known to those of skill in the art. Examples of suitable deposition methods include without limitation, conventional chemical vapor deposition (CVD), low pressure chemical vapor deposition (LPCVD), atomic layer deposition (ALD), pulsed chemical vapor deposition (P-CVD), plasma enhanced atomic layer deposition (PE-ALD), or combinations thereof. Preferably, the deposition method is ALD or PE-ALD.

The vapor of the hafnium-containing or zirconium-containing precursor is introduced into a reaction chamber containing at least one substrate. The temperature and the pressure within the reaction chamber and the temperature of the substrate are held at suitable conditions so that contact between the hafnium-containing or zirconium-containing precursor and substrate results in formation of a Hf-containing or Zr-containing layer on at least one surface of the substrate. A reactant may also be used to help in formation of the Hf-containing or Zr-containing layer.

The reaction chamber may be any enclosure or chamber of a device in which deposition methods take place, such as, without limitation, a parallel-plate type reactor, a cold-wall type reactor, a hot-wall type reactor, a single-wafer reactor, a multi-wafer reactor, or other such types of deposition systems. All of these exemplary reaction chambers are capable of serving as an ALD reaction chamber. The reaction chamber may be maintained at a pressure ranging from about 0.5 mTorr (0.07 Pa) to about 20 Torr (2700 Pa). In addition, the temperature within the reaction chamber may range from about 200° C. to about 600° C. One of ordinary skill in the art will recognize that the temperature may be optimized through mere experimentation to achieve the desired result.

The temperature of the reaction chamber may be controlled by either controlling the temperature of the substrate holder or controlling the temperature of the reactor wall. Devices used to heat the substrate are known in the art. The reactor wall is heated to a sufficient temperature to obtain the desired film at a sufficient growth rate and with desired physical state and composition. A non-limiting exemplary temperature range to which the reactor wall may be heated includes from approximately 200° C. to approximately 600° C. When a plasma deposition process is utilized, the deposition temperature may range from approximately 200° C. to approximately 550° C. Alternatively, when a thermal process is performed, the deposition temperature may range from approximately 400° C. to approximately 600° C.

Alternatively, the substrate may be heated to a sufficient temperature to obtain the desired hafnium-containing or zirconium-containing film at a sufficient growth rate and with desired physical state and composition. A non-limiting exemplary temperature range to which the substrate may be heated includes from 150° C. to 600° C. Preferably, the temperature of the substrate remains less than or equal to 450° C.

The type of substrate upon which the hafnium-containing or zirconium-containing film will be deposited will vary depending on the final use intended. In some embodiments, the substrate may be chosen from oxides which are used as dielectric materials in MIM, DRAM, or FeRam technologies (for example, $HfO_2$ based materials, $TiO_2$ based materials, $ZrO_2$ based materials, rare earth oxide based materials, ternary oxide based materials, etc.) or from nitride-based films (for example, TaN) that are used as an oxygen barrier between copper and the low-k layer. Other substrates may be used in the manufacture of semiconductors, photovoltaics, LCD-TFT, or flat panel devices. Examples of such substrates include, but are not limited to, solid substrates such as metal nitride containing substrates (for example, TaN, TiN, WN, TaCN, TiCN, TaSiN, and TiSiN); insulators (for example, $SiO_2$, $Si_3N_4$, SiON, $HfO_2$, $Ta_2O_5$, $ZrO_2$, $TiO_2$, $Al_2O_3$, and barium strontium titanate); or other substrates that include any number of combinations of these materials. The actual substrate utilized may also depend upon the specific precursor embodiment utilized. In many instances though, the preferred substrate utilized will be selected from TiN, SRO, Ru, and Si type substrates.

The hafnium-containing or zirconium-containing precursor may be fed in liquid state to a vaporizer where it is vaporized before it is introduced into the reaction chamber. Prior to its vaporization, the hafnium-containing or zirconium-containing precursor may optionally be mixed with one or more solvents, one or more metal sources, and a mixture of one or more solvents and one or more metal sources. The solvents may be selected from the group consisting of toluene, ethyl benzene, xylene, mesitylene, decane, dodecane, octane, hexane, pentane, or others. The resulting concentration may range from approximately 0.05 M to approximately 2 M. The metal source may include any metal-containing precursors now known or later developed.

Alternatively, the hafnium-containing or zirconium-containing precursor may be vaporized by passing a carrier gas into a container containing the hafnium-containing or zirconium-containing precursor or by bubbling the carrier gas into the hafnium-containing or zirconium-containing precursor. The carrier gas and hafnium-containing or zirconium-containing precursor are then introduced into the reaction chamber as a vapor. The carrier gas may include, but is not limited to, Ar, He, $N_2$, and mixtures thereof. The hafnium-containing or zirconium-containing precursor may optionally be mixed in the container with one or more solvents, metal-containing precursors, or mixtures thereof. If necessary, the container may be heated to a temperature that permits the hafnium-containing or zirconium-containing precursor to be in its liquid phase and to have a sufficient vapor pressure. The container may be maintained at temperatures in the range of, for example, approximately 0° C. to approximately 150° C. Those skilled in the art recognize that the temperature of the container may be adjusted in a known manner to control the amount of hafnium-containing or zirconium-containing precursor vaporized.

In addition to the optional mixing of the hafnium-containing or zirconium-containing precursor with solvents, metal-containing precursors, and stabilizers prior to introduction into the reaction chamber, the hafnium-containing or zirconium-containing precursor may be mixed with reactants inside the reaction chamber. Exemplary reactants include, without limitation, metal-containing precursors such as aluminum-containing precursors such as TMA or silicon-containing precursors such as bis(diethylamino)silane. These or other metal-containing precursors may be incorporated into the resultant film in small quantities, as a dopant, or as a second or third metal in the resulting film, such as PZT.

When the desired hafnium-containing or zirconium-containing film also contains oxygen, such as, for example and without limitation, ZrO, the reactants may include an oxygen source which is selected from, but not limited to, $O_2$, $O_3$, $H_2O$, $H_2O_2$, acetic acid, formalin, para-formaldehyde, and combinations thereof. Preferably, when an ALD process is performed, the reactant is $H_2O$.

The reactant may be treated by plasma in order to decompose the reactant into its radical form. The plasma may be generated or present within the reaction chamber itself. Alternatively, the plasma may generally be at a location removed from the reaction chamber, for instance, in a remotely located plasma system. One of skill in the art will recognize methods and apparatus suitable for such plasma treatment.

For example, the reactant may be introduced into a direct plasma reactor, which generates a plasma in the reaction chamber, to produce the plasma-treated reactant in the reaction chamber. Exemplary direct plasma reactors include the Titan™ PECVD System produced by Trion Technologies. The reactant may be introduced and held in the reaction chamber prior to plasma processing. Alternatively, the plasma processing may occur simultaneously with the introduction of reactant. In-situ plasma is typically a 13.56 MHz RF capacitively coupled plasma that is generated between the showerhead and the substrate holder. The substrate or the showerhead may be the powered electrode depending on whether positive ion impact occurs. Typical applied powers in in-situ plasma generators are from approximately 100 W to approximately 1000 W. The disassociation of the reactant using in-situ plasma is typically less than achieved using a remote plasma source for the same power input and is therefore not as efficient in reactant disassociation as a remote plasma system, which may be beneficial for the deposition of metal-nitride-containing films on substrates easily damaged by plasma.

Alternatively, the plasma-treated reactant may be produced outside of the reaction chamber. The MKS Instruments' ASTRON® i reactive gas generator may be used to treat the reactant prior to passage into the reaction chamber. Operated at 2.45 GHz, 7 kW plasma power, and a pressure ranging from approximately 3 Torr to approximately 10 Torr, the reactant $O_3$ may be decomposed into three $O^-$ radicals. Preferably, the remote plasma may be generated with a power ranging from about 1 kW to about 10 kW, more preferably from about 2.5 kW to about 7.5 kW.

When the desired hafnium-containing or zirconium-containing film also contains another metal, such as, for example and without limitation, Ta, Hf, Zr, Nb, Mg, Al, Sr, Y, Ba, Ca, As, Sb, Bi, Sn, Pb, Co, lanthanides (such as Eu), or combinations thereof, the reactants may include a metal-containing precursor which is selected from, but not limited to, metal alkyls, such as $Ln(RCp)_3$ or $Co(RCp)_2$, metal alkoxies, such as $Ti(Cp)(OMe)_3$, and any combination thereof.

The vapor of the metal-containing precursor is introduced into a reaction chamber. The temperature and the pressure within the reaction chamber and the temperature of the substrate are held at suitable conditions so that contact between the metal-containing precursor and substrate results in formation of a metal-containing layer on at least one surface of the substrate. A reactant may also be used to help in formation of the metal-containing layer.

One of ordinary skill in the art will recognize that additional reactants may be used in the disclosed deposition processes.

The hafnium-containing or zirconium-containing precursor and one or more reactants may be introduced into the reaction chamber simultaneously (chemical vapor deposition), sequentially (atomic layer deposition), or in other combinations. For example, the hafnium-containing or zirconium-containing precursor may be introduced in one pulse and two additional metal sources may be introduced together in a separate pulse [modified atomic layer deposition]. Alternatively, the reaction chamber may already contain the reactant prior to introduction of the hafnium-containing or zirconium-containing precursor. The reactant may be passed through a plasma system localized remotely from the reaction chamber, and decomposed to radicals. Alternatively, the hafnium-containing or zirconium-containing precursor may be introduced to the reaction chamber continuously while other metal sources are introduced by pulse (pulsed-chemical vapor deposition). In each example, a pulse may be followed by a purge or evacuation step to remove excess amounts of the component introduced. In each example, the pulse may last for a time period ranging from about 0.01 s to about 10 s, alternatively from about 0.3 s to about 3 s, alternatively from about 0.5 s to about 2 s.

In one non-limiting exemplary atomic layer deposition type process, the vapor phase of a hafnium-containing or zirconium-containing precursor is introduced into the reaction chamber, where it is contacted with a suitable substrate. Excess hafnium-containing or zirconium-containing precursor may then be removed from the reaction chamber by purging and/or evacuating the reaction chamber. An oxygen source is introduced into the reaction chamber where it reacts with the absorbed hafnium-containing or zirconium-containing precursor in a self-limiting manner. Any excess oxygen source is removed from the reaction chamber by purging and/or evacuating the reaction chamber. If the desired film is a hafnium oxide or zirconium oxide film, this two-step process may provide the desired film thickness or may be repeated until a film having the necessary thickness has been obtained.

Alternatively, if the desired film is a hafnium or zirconium metal oxide film, the two-step process above may be followed by introduction of a second vapor of a metal-containing precursor into the reaction chamber. The metal-containing precursor will be selected based on the nature of the hafnium metal oxide or zirconium metal oxide film being deposited. After introduction into the reaction chamber, the metal-containing precursor is contacted with the substrate. Any excess metal-containing precursor is removed from the reaction chamber by purging and/or evacuating the reaction chamber. Once again, an oxygen source may be introduced into the reaction chamber to react with the metal-containing precursor. Excess oxygen source is removed from the reaction chamber by purging and/or evacuating the reaction chamber. If a desired film thickness has been achieved, the process may be terminated. However, if a thicker film is desired, the entire four-step process may be repeated. By alternating the provision of the hafnium-containing or zirconium-containing precursor, metal-containing precursor, and oxygen source, a film of desired composition and thickness can be deposited.

Additionally, by varying the number of pulses, films having a desired stoichiometric Hf:metal or Zr:metal ratio may be obtained. For example, a PZT film ($Pb[Zr_xTi_{1-x}]O_3$ with $0<x<1$) may be obtained by having one pulse of the zirconium-containing precursor, one pulse of a titanium-containing precursor, and two pulses of the lead-containing precursor, with each pulse being followed by pulses of the oxygen source. However, one of ordinary skill in the art will recognize that the number of pulses required to obtain the desired film may not be identical to the stoichiometric ratio of the resulting film.

The hafnium-containing or zirconium-containing films resulting from the processes discussed above may include PZT. One of ordinary skill in the art will recognize that by judicial selection of the appropriate hafnium-containing or zirconium-containing precursor and reactants, the desired film composition may be obtained.

EXAMPLES

The following non-limiting examples are provided to further illustrate embodiments of the invention. However, the examples are not intended to be all inclusive and are not intended to limit the scope of the inventions described herein.

Prophetic Example 1

$Hf(N^{iPr}\text{-amd})(OiPr)_3$ or $Zr(N^{iPr}\text{-amd})(OiPr)_3$: A pentane solution will be chilled to $-30°$ C. for 1 hour. $Hf(OiPr)_3(NMe_2)$ or $Zr(OiPr)_3(NMe_2)$ will be added to the chilled pentane solution. The mixture will be stirred at room temperature under atmosphere of nitrogen. A solution of $N^{iPr}$-amd-H in pentane will slowly be added to the above mixture. The outlet of the flask will be connected to an oil bubbler, which in turn will be connected to an acid scrubber. The resulting solution will be stirred at room temperature overnight. Solvent and volatiles will be removed from the reaction mixture under vacuum, resulting in the target molecule ($Hf(N^{iPr}\text{-amd})(OiPr)_3$ or $Zr(N^{iPr}\text{-amd})(OiPr)_3$).

Prophetic Example 2

$Hf(N^{iPr}\text{-amd})_2(OiPr)_2$ or $Zr(N^{iPr}\text{-amd})_2(OiPr)_2$: Neat $Hf(OiPr)_2(NMe_2)_2$ or neat $Zr(OiPr)_2(NMe_2)_2$ will be added to a pentane solution containing $N^{iPr}$-amd-H stirring at room temperature under atmosphere of nitrogen, the outlet of the flask will be connected to an oil bubbler. The resulting solution will be stirred at room temperature overnight. Solvent and volatiles will be removed from the reaction mixture under vacuum, resulting in the target molecule ($Hf(N^{iPr}\text{-amd})_2(OiPr)_2$ or $Zr(N^{iPr}\text{-amd})_2(OiPr)_2$).

Prophetic Example 3

$Hf(N^{iPr}\text{-fmd})_2(OiPr)_2$ or $Zr(N^{iPr}\text{-fmd})_2(OiPr)_2$: Neat $Hf(OiPr)_2(NMe_2)_2$ or neat $Zr(OiPr)_2(NMe_2)_2$ will be added to a pentane solution containing $N^{iPr}$-fmd-H stirring at room temperature under atmosphere of nitrogen, the outlet of the flask will be connected to an oil bubbler. The resulting solution will be stirred at room temperature overnight. Solvent and volatiles will be removed from the reaction mixture under vacuum, resulting in the target molecule ($Hf(N^{iPr}\text{-fmd})_2(OiPr)_2$ or $Zr(N^{iPr}\text{-fmd})_2(OiPr)_2$).

Prophetic Example 4

$Hf(N^{iPr}\text{-gmd})_2(OiPr)_2$ or $Zr(N^{iPr}\text{-gmd})_2(OiPr)_2$: Neat $Hf(OiPr)_2(NMe_2)_2$ or neat $Zr(OiPr)_2(NMe_2)_2$ will be added to a pentane solution containing iPr-N=C=N-iPr stirring at room temperature under atmosphere of nitrogen, the outlet of the flask will be connected to an oil bubbler. The resulting solution will be stirred at room temperature overnight. Solvent and volatiles will be removed from the reaction mixture under vacuum, resulting in the target molecule ($Hf(N^{iPr}\text{-gmd})_2(OiPr)_2$ or $Zr(N^{iPr}\text{-gmd})_2(OiPr)_2$).

Prophetic Example 5

$Hf(N^{iPr}\text{-amd})(OiPr)_2(NMe_2)$ or $Zr(N^{iPr}\text{-amd})(OiPr)_2(NMe_2)$: A solution of $N^{iPr}$-amd-H in pentane will be added slowly dropwise to a pentane solution containing $Hf(OiPr)_2(NMe_2)_2$ or $Zr(OiPr)_2(NMe_2)_2$ stirring at room temperature under atmosphere of nitrogen. The outlet of the flask will be connected to an oil bubbler, which in turn will be connected to an acid scrubber. The resulting solution will be stirred at room temperature overnight. Solvent and volatiles will be removed from the reaction mixture under vacuum, resulting in the target molecule ($Hf(N^{iPr}\text{-amd})(OiPr)_2(NMe_2)$ or $Zr(N^{iPr}\text{-amd})(OiPr)_2(NMe_2)$).

Prophetic Example 6

$Hf(Et\text{-}N\text{---}(CH_2)_2\text{---}N\text{-}Et)(OiPr)_2$ or $Zr(Et\text{-}N\text{---}(CH_2)_2\text{---}N\text{-}Et)(OiPr)_2$: To a pentane solution containing $Hf(OiPr)_2(NMe_2)_2$ or $Zr(OiPr)_2(NMe_2)_2$ stirring at room temperature under atmosphere of nitrogen will be added slowly drop wise neat liquid of $Et\text{-}NH\text{---}(CH_2)_2\text{---}NH\text{-}Et$. The outlet of the flask will be connected to an oil bubbler, which in turn will be connected to an acid scrubber. The resulting solution will be stirred at room temperature overnight. Solvent and volatiles will be removed from the reaction mixture under vacuum, resulting in the target molecule ($Hf(Et\text{-}N\text{---}(CH_2)_2\text{---}N\text{-}Et)(OiPr)_2$ or $Zr(Et\text{-}N\text{---}(CH_2)_2\text{---}N\text{-}Et)(OiPr)_2$).

Prophetic Example 7

$Ti(Me\text{-}N\text{---}(CH_2)_2\text{---}N\text{-}Me)(OiPr)_2$: Synthesis will be carried out similar to Example 6 with reactants having the appropriate ligands.

Prophetic Example 8

$Ti(Me_2CH\text{---}N\text{---}(CH_2)_3\text{---}N\text{---}CHMe_2)(OiPr)_2$: Synthesis will be carried out similar to Example 6 with reactants having the appropriate ligands.

Prophetic Example 9

The hafnium-containing or zirconium-containing precursor of any one of Examples 1 to 8 and the reactant $O_3$ will be used to deposit a film of $HfO_2$ or $ZrO_2$ on a $SiO_2/Si$ substrate. The $SiO_2/Si$ substrate will be maintained at a temperature of 250° C. The precursor will be vaporized in a bubbler maintained at 50° C. The ALD cycle will include a precursor pulse of 5 seconds, followed by a 5 second purge, followed by a reactant pulse of 2 seconds, followed by a 5 second purge. The HfO$_2$ or ZrO$_2$ growth rate is expected to be 0.5 Å/cycle or greater. The ALD regime will be assessed up to 350° C. with a deposition rate.

Prophetic Example 10

The hafnium-containing or zirconium-containing precursor of any one of Examples 1 to 8 and the reactant H$_2$O will be used to deposit a film of HfO$_2$ or ZrO$_2$ on a SiO$_2$/Si substrate. The SiO$_2$/Si substrate will be maintained at a temperature of 250° C. The precursor will be vaporized in a bubbler maintained at 50° C. The ALD cycle will include a precursor pulse of 20 seconds, followed by a 5 second purge, followed by a reactant pulse of 2 seconds, followed by a 10 second purge. The HfO$_2$ or ZrO$_2$ growth rate is expected to be 0.5 Å/cycle or greater. The ALD regime will be assessed up to 350° C.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

What is claimed is:

1. A molecule having the following formula:

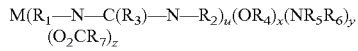

Formula I or

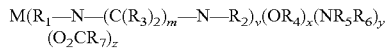

Formula II wherein:
M is Hf or Zr;
R$_1$, R$_2$, R$_5$, R$_6$, and R$_7$ are independently selected from the group consisting of H and C1-C6 alkyl group;
R$_3$=H, C1-C6 alkyl group, or NMe$_2$;
R$_4$ is a C1-C6 alkyl group;
m=2-4;
u=0-2;
V=0;
X=1-3;
y=0-2;
z=0-1;
in Formula I, u+x+y+z=4;
in Formula II, 2v+x+y+z=4; and
u, v, or z≥1.

2. The molecule of claim 1, the molecule having Formula I, wherein u=1, x=3, y=0, and z=0.

3. The molecule of claim 2, wherein the molecule is selected from the group consisting of M(iPr-N—C(Me)-N-iPr)$_1$(OiPr)$_3$, M(iPr-N—C(Me)-N-iPr)$_1$(OMe)$_3$, M(iPr-N—C(Me)-N-iPr)$_1$(OEt)$_3$, M(iPr-N—C(Me)-N-iPr)$_1$(OnPr)$_3$, M(iPr-N—C(Me)-N-iPr)$_1$(OsBu)$_3$, M(iPr-N—C(Me)-N-iPr)$_1$(OiBu)$_3$, M(iPr-N—C(Me)—N-iPr)$_1$(OtBu)$_3$, M(Et-N—C(Me)-N-Et)$_1$(OEt)$_3$, M(Et-N—C(Me)-N-Et)$_1$(OMe)$_3$, M(Et-N—C(Me)-N-Et)$_1$(OnPr)$_3$, M(Et-N—C(Me)-N-Et)$_1$(OsBu)$_3$, M(Et-N—C(Me)-N-Et)$_1$(OiBu)$_3$, M(Et-N—C(Me)-N-Et)$_1$(OtBu)$_3$, and M(iPr-N—C(NMe$_2$)—N-iPr)(OiPr)$_3$.

4. The molecule of claim 1, the molecule having Formula II, wherein v=1, x=2, y=0, and z=0.

5. The molecule of claim 4, wherein the molecule is selected from the group consisting of M(iPr-N—(CH$_2$)$_2$—N-iPr)$_1$(OiPr)$_2$, M(iPr-N—(CH$_2$)$_2$—N-iPr)$_1$(OMe)$_2$, M(iPr-N—(CH$_2$)$_2$—N-iPr)$_1$(OEt)$_2$, M(iPr-N—(CH$_2$)$_2$—N-iPr)$_1$(OnPr)$_2$, M(iPr-N—(CH$_2$)$_2$—N-iPr)$_1$(OsBu)$_2$, M(iPr-N—(CH$_2$)$_2$—N-iPr)$_1$(OiBu)$_2$, M(iPr-N—(CH$_2$)$_2$—N-iPr)$_1$(OtBu)$_2$, M(Et-N—(CH$_2$)$_2$—N-Et)$_1$(OiPr)$_2$, M(Et-N—(CH$_2$)$_2$—N-Et)$_1$(OMe)$_2$, M(Et-N—(CH$_2$)$_2$—N-Et)$_1$(OEt)$_2$, M(Et-N—(CH$_2$)$_2$—N-Et)$_1$(OnPr)$_2$, M(Et-N—(CH$_2$)$_2$—N-Et)$_1$(OsBu)$_2$, M(Et-N—(CH$_2$)$_2$—N-Et)$_1$(OiBu)$_2$, M(Et-N—(CH$_2$)$_2$—N-Et)$_1$(OtBu)$_2$, M(iPr-N—(CH$_2$)$_3$—N-iPr)$_1$(OiPr)$_2$, M(iPr-N—(CH$_2$)$_3$—N-iPr)$_1$(OMe)$_2$, M(iPr-N—(CH$_2$)$_3$—N-iPr)$_1$(OEt)$_2$, M(iPr-N—(CH$_2$)$_3$—N-iPr)$_1$(OnPr)$_2$; M(iPr-N—(CH$_2$)$_3$—N-iPr)$_1$(OsBu)$_2$, M(iPr-N—(CH$_2$)$_3$—N-iPr)$_1$(OiBu)$_2$, M(iPr-N—(CH$_2$)$_3$—N-iPr)$_1$(OtBu)$_2$, M(Et-N—(CH$_2$)$_3$—N-Et)$_1$(OiPr)$_2$, M(Et-N—(CH$_2$)$_3$—N-Et)$_1$(OMe)$_2$, M(Et-N—(CH$_2$)$_3$—N-Et)$_1$(OEt)$_2$, M(Et-N—(CH$_2$)$_3$—N-Et)$_1$(OnPr)$_2$, M(Et-N—(CH$_2$)$_3$—N-Et)$_1$(OsBu)$_2$, M(Et-N—(CH$_2$)$_3$—N-Et)$_1$(OiBu)$_2$, and M(Et-N—(CH$_2$)$_3$—N-Et)$_1$(OtBu)$_2$.

6. The molecule of claim 1, the molecule having Formula I, wherein u=2, x=2, y=0, and z=0.

7. The molecule of claim 6, wherein the molecule is selected from the group consisting of M(iPr-N—C(H)—N-iPr)$_2$(OiPr)$_2$, M(iPr-N—C(H)—N-iPr)$_2$(OMe)$_2$, M(iPr-N—C(H)—N-iPr)$_2$(OEt)$_2$, M(iPr-N—C(H)—N-iPr)$_2$(OnPr)$_2$, M(iPr-N—C(H)—N-iPr)$_2$(OsBu)$_2$, M(iPr-N—C(H)—N-iPr)$_2$(OiBu)$_2$, M(iPr-N—C(H)—N-iPr)$_2$(OtBu)$_2$, M(Et-N—C(H)—N-Et)$_2$(OiPr)$_2$, M(Et-N—C(H)—N-Et)$_2$(OMe)$_2$, M(Et-N—C(H)—N-Et)$_2$(OEt)$_2$, M(Et-N—C(H)—N-Et)$_2$(OnPr)$_2$, M(Et-N—C(H)—N-Et)$_2$(OsBu)$_2$, M(Et-N—C(H)—N-Et)$_2$(OiBu)$_2$, M(Et-N—C(H)—N-Et)$_2$(OtBu)$_2$, M(iPr-N—C(Me)-N-iPr)$_2$(OiPr)$_2$, M(iPr-N—C(Me)-N-iPr)$_2$(OMe)$_2$, M(iPr-N—C(Me)-N-iPr)$_2$(OEt)$_2$, M(iPr-N—C(Me)-N-iPr)$_2$(OnPr)$_2$, M(iPr-N—C(Me)-N-iPr)$_2$(OsBu)$_2$, M(iPr-N—C(Me)-N-iPr)$_2$(OsBu)$_2$, M(iPr-N—C(Me)-N-iPr)$_2$(OiBu)$_2$, M(iPr-N—C(Me)-N-Et)$_2$(OtBu)$_2$, M(Et-N—C(Me)-N-Et)$_2$(OiPr)$_2$, M(Et-N—C(Me)-N-Et)$_2$(OMe)$_2$, M(Et-N—C(Me)-N-Et)$_2$(OEt)$_2$, M(Et-N—C(Me)-N-Et)$_2$(OnPr)$_2$, M(Et-N—C(Me)-N-Et)$_2$(OsBu)$_2$, M(Et-N—C(Me)-NEt)$_2$,(OiBu)$_2$, and M(Et-N—C(Me)-N-Et)$_2$(OtBu)$_2$.

8. The molecule of claim 1, the molecule having Formula I, wherein u=1, x=2, y=1, and z=0.

9. The molecule of claim 8, wherein the molecule is selected from the group consisting of M(iPr-N—C(Me)-N-iPr)(OiPr)$_2$(NMe$_2$), M(iPr-N—C(Me)-N-iPr)(OiPr)$_2$(NEt$_2$), M(iPr-N—C(Me)-N-iPr)(OiPr)$_2$(NEtMe), M(Et-N—C(Me)-N-Et)(OiPr)$_2$(NMe$_2$), M(Et-N—C(Me)-N-Et)(OiPr)$_2$(NEt$_2$), M(Et-N—C(Me)-N-Et)(OiPr)$_2$(NEtMe), M(iPr-N—C(NMe$_2$)—N-iPr)(OiPr)$_2$(NMe$_2$), M(iPr-N—C(NMe$_2$)—N-iPr)(OiPr)$_2$(NEt$_2$), M(iPr-N—C(NMe$_2$)—N-iPr)(OiPr)$_2$(NEtMe), M(iPr-N—C(Me)—N-iPr)(OiPr)$_2$(NMeiPr), M(iPr-N—C(Me)-N-iPr)(OiPr)$_2$(NiPr$_2$), M(iPr-N—C(Me)-N-iPr)(OiPr)$_2$(NMetBu), M(iPr-N—C(Me)-N-iPr)(OiPr)$_2$(NneoPentyl$_2$), M(Et-N—C(Me)-N-Et)(OiPr)$_2$(NMeiPr), M(Et-N—C(Me)-N-Et)(OiPr)$_2$(NiPr$_2$), M(Et-N—C(Me)-N-Et)(OiPr)$_2$(NneoPentyl$_2$), M(iPr-N—C(NMe$_2$)—N-iPr)(OiPr)$_2$(NMeiPr),M(iPr-N—C(NMe$_2$)—N-iPr)(OiPr)$_2$(NiPr$_2$), M(iPr-N—C(NMe$_2$)—N-iPr)(OiPr)$_2$(NneoPentyl$_2$) and M(iPr-N—C(NMe$_2$)—N-iPr)(OiPr)$_2$(NMeiPr).

10. The molecule of claim 1, the molecule having Formula I, wherein u=1, x=2, y=0, and z=1.

11. The molecule of claim 10, wherein the molecule is selected from the group consisting of M(iPr-N—C(Me)-N-iPr)(OiPr)$_2$(O$_2$CMe) and M(Et-N—C(Me)-N-Et)(OiPr)$_2$(O$_2$CMe).

12. The molecule of claim 1, the molecule having Formula II, wherein v=1, x=1, y=0, and z=1.

13. The molecule of claim 12, wherein the molecule is selected from the group consisting of M(iPr-N—(CH$_2$)$_2$—N-iPr)(OiPr)(O$_2$CMe), M(iPr-N—(CH$_2$)$_2$—N-iPr)(OMe)(O$_2$CMe), M(iPr-N—(CH$_2$)$_2$—N-iPr)(OEt)(O$_2$CMe), M(iPr-N—(CH$_2$)$_2$—N-iPr)(OnPr)(O$_2$CMe), M(iPr-N—(CH$_2$)$_2$—N-iPr)(OsBu)(O$_2$CMe), M(iPr-N—(CH$_2$)$_2$—N-iPr)(OiBu)(O$_2$CMe), M(iPr-N—(CH$_2$)$_2$—N-iPr)(OtBu)(O$_2$CMe), M(Et-N—(CH$_2$)$_2$—N-Et)(OiPr)(O$_2$CMe), M(Et-N—(CH$_2$)$_2$—N-Et)(OMe)(O$_2$CMe), M(Et-N—(CH$_2$)$_2$—N-Et)(OEt)(O$_2$CMe), M(Et-N—(CH$_2$)$_2$—N-Et)(OnPr)(O$_2$CMe), M(Et-N—(CH$_2$)$_2$—N-Et)(OsBu)(O$_2$CMe), M(Et-N—(CH$_2$)$_2$—N-Et)(OiBu)(O$_2$CMe), and M(Et-N—(CH$_2$)$_2$—N-Et)(OtBu)(O$_2$CMe).

14. The molecule of claim 1, the molecule having either Formula I or Formula II, wherein u, v, y=0, x=2, and z=2.

15. The molecule of claim 14, the molecule being M(OiPr)$_2$ (O$_2$CMe)$_2$.

16. The molecule of claim 1, the molecule having either Formula I or Formula II, wherein u, v, y=0, x=3, and z=1.

17. The molecule of claim 16, the molecule being M(OiPr)$_3$ (O$_2$CMe).

18. A method of forming a Hf-containing or Zr-containing layer on a substrate, the method comprising:
providing a reaction chamber having at least one substrate disposed therein;
introducing into the reaction chamber a vapor including at least one precursor having the formula:

$$M(R_1—N—C(R_3)—N—R_2)_u(OR_4)_x(NR_5R_6)_y(O_2CR_7)_z \quad \text{Formula I}$$

or $$M(R_1—N—(C(R_3)_2)_m—N—R_2)_v(OR_4)_x(NR_5R_6)_y(O_2CR_7)_z \quad \text{Formula II}$$

wherein:
M is Hf or Zr;
R$_1$, R$_2$, R$_5$, R$_6$, and R$_7$ are independently selected from the group consisting of H and C1-C6 alkyl group;
R$_3$=H, C1-C6 alkyl group, or NMe$_2$;
R$_4$ is a C1-C6 alkyl group;
m=2-4;
u=0-2;
v=0-1;
x=1-3;
y=0-2;
z=0-1;
in Formula I, u+x+y+z=4;
in Formula II 2v+x+y+z=4; and
u, v, or z≥1;
contacting the vapor with the substrate to form the Hf-containing or Zr-containing layer on at least one surface of the substrate using a vapor deposition process.

19. The method of claim 18, wherein the at least one precursor is selected from the group consisting of M(iPr-N—C(Me)-N-iPr)$_1$(OiPr)$_3$, M(iPr-N—C(Me)-N-iPr)$_1$(OMe)$_3$, M(iPr-N—C(Me)-N-iPr)$_1$(OEt)$_3$, M(iPr-N—C(Me)-N-iPr)$_1$(OnPr)$_3$, M(iPr-N—C(Me)-N-iPr)$_1$(OsBu)$_3$, M(iPr-N—C(Me)-N-iPr)$_1$(OiBu)$_3$, M(iPr-N—C(Me)—N-iPr)$_1$(OtBu)$_3$, M(Et-N—C(Me)-N-Et)$_1$(OEt)$_3$, M(Et-N—C(Me)-N-Et)$_1$(OMe)$_3$, M(Et-N—C(Me)-N-Et)$_1$(OnPr)$_3$, M(Et-N—C(Me)-N-Et)$_1$(OsBu)$_3$, M(Et-N—C(Me)-N-Et)$_1$(OiBu)$_3$, M(Et-N—C(Me)-N-Et)$_1$(OtBu)$_3$, M(iPr-N—C(NMe$_2$)—N-iPr)(OiPr)$_3$, M(iPr-N—(CH$_2$)$_2$—N-iPr)$_1$(OiPr)$_2$, M(iPr-N—(CH$_2$)$_2$—N-iPr)$_1$(OMe)$_2$, M(iPr-N—(CH$_2$)$_2$—N-iPr)$_1$(OEt)$_2$, M(iPr-N—(CH$_2$)$_2$—N-iPr)$_1$(OnPr)$_2$, M(iPr-N—(CH$_2$)$_2$—N-iPr)$_1$(OsBu)$_2$, M(iPr-N—(CH$_2$)$_2$—N-iPr)$_1$(OiBu)$_2$, M(iPr-N—(CH$_2$)$_2$—N-iPr), (OtBu)$_2$, M(Et-N—(CH$_2$)$_2$—N-Et)$_1$(OiPr)$_2$, M(Et-N—(CH$_2$)$_2$—N-Et)$_1$(OMe)$_2$, M(Et-N—(CH$_2$)$_2$—N-Et)$_1$(OEt)$_2$, M(Et-N—(CH$_2$)$_2$—N-Et)$_1$(OnPr)$_2$, M(Et-N—(CH$_2$)$_2$—N-Et)$_1$(OsBu)$_2$, M(Et-N—(CH$_2$)$_2$—N-Et)$_1$(OiBu)$_2$, M(Et-N—(CH$_2$)$_2$—N-Et)$_1$(OtBu)$_2$, M(iPr-N—(CH$_2$)$_3$—N-iPr)$_1$(OiPr)$_2$, M(iPr-N—(CH$_2$)$_3$—N-iPr)$_1$(OMe)$_2$, M(iPr-N—(CH$_2$)$_3$—N-iPr)$_1$(OEt)$_2$, M(iPr-N—(CH$_2$)$_3$—N-iPr)$_1$(OnPr)$_2$, M(iPr-N—(CH$_2$)$_3$—N-iPr)$_1$(OsBu)$_2$, M(iPr-N—(CH$_2$)$_3$—N-iPr)$_1$(OiBu)$_2$, M(iPr-N—(CH$_2$)$_3$—N-iPr)$_1$(OtBu)$_2$, M(Et-N—(CH$_2$)$_3$—N-Et)$_1$(OiPr)$_2$, M(Et-N—(CH$_2$)$_3$—N-Et)$_1$(OMe)$_2$, M(Et-N—(CH$_2$)$_3$—N-Et)$_1$(OEt)$_2$, M(Et-N—(CH$_2$)$_3$—N-Et)$_1$(OnPr)$_2$, M(Et-N—(CH$_2$)$_3$—N-Et)$_1$(OsBu)$_2$, M(Et-N—(CH$_2$)$_3$—N-Et)$_1$(OiBu)$_2$, M(Et-N—(CH$_2$)$_3$—N-Et)$_1$(OtBu)$_2$, M(iPr-N—C(H)—N-iPr)$_2$(OiPr)$_2$, M(iPr-N—C(H)—N-iPr)$_2$(OMe)$_2$, M(iPr-N—C(H)—N-iPr)$_2$(OEt)$_2$, M(iPr-N—C(H)—N-iPr)$_2$(OnPr)$_2$, M(iPr-N—C(H)—N-iPr)$_2$(OsBu)$_2$, M(iPr-N—C(H)—N-iPr)$_2$(OiBu)$_2$, M(iPr-N—C(H)—N-iPr)$_2$(OtBu)$_2$, M(Et-N—C(H)—N-Et)$_2$(OiPr)$_2$, M(Et-N—C(H)—N-Et)$_2$(OMe)$_2$, M(Et-N—C(H)—N-Et)$_2$(OEt)$_2$, M(Et-N—C(H)—N-Et)$_2$(OnPr)$_2$, M(Et-N—C(H)—N-Et)$_2$(OsBu)$_2$, M(Et-N—C(H)—N-Et)$_2$(OiBu)$_2$, M(Et-N—C(H)—N-Et)$_2$(OtBu)$_2$, M(iPr-N—C(Me)-N-iPr)$_2$(OiPr)$_2$, M(iPr-N—C(Me)-N-iPr)$_2$(OMe)$_2$, M(iPr-N—C(Me-N-iPr)$_2$(OEt)$_2$, M(iPr-N—C(Me)-N-iPr)$_2$(OnPr)$_2$, M(iPr-N—C(Me)-N-iPr)$_2$(OsBu)$_2$, M(iPr-N—C(Me)-N-iPr)$_2$(OiBu)$_2$, M(iPr-N—C(Me)-N-iPr)$_2$(OtBu)$_2$, M(Et-N—C(Me)-N-Et)$_2$(OiPr)$_2$, M(Et-N—C(Me)-N-Et)$_2$(OMe)$_2$, M(Et-N—C(Me)-N-Et)$_2$(OEt)$_2$, M(Et-N—C(Me)-N-Et)$_2$(OnPr)$_2$, M(Et-N—C(Me)-N-Et)$_2$(OsBu)$_2$, M(Et-N—C(Me)-N-Et)$_2$(OiBu)$_2$, M(Et-N—C(Me)-N-Et)$_2$(OtBu)$_2$, M(iPr-N—C(Me-N-iPr)(OiPr)$_2$(NMe$_2$), M(iPr-N—C(Me)-N-iPr)(OiPr)$_2$(NEt$_2$), M(iPr-N—C(Me)-N-iPr)(OiPr)$_2$(NEtMe), M(Et-N—C(Me)-N-Et)(OiPr)$_2$(NMe$_2$), M(Et-N—C(Me)-N-Et)(OiPr)$_2$(NEt$_2$), M(Et-N—C(Me)-N-Et)(OiPr)$_2$(NEtMe), M(iPr-N—C(NMe$_2$)—N-Pr)(OiPr)$_2$(NMe$_2$), M(iPr-N—C(NMe$_2$)—N-iPr)(OiPr)$_2$(NEt$_2$), M(iPr-N—C(NMe$_2$)—N-iPr)(OiPr)$_2$(NEtMe), M(iPr-N—C(Me)—N-Pr)(OiPr)$_2$(O$_2$CMe), M(Et-N—C(Me)-N-Et)(OiPr)$_2$(O$_2$CMe), M(iPr-N—(CH$_2$)$_2$—N-iPr)(OiPr)(O$_2$CMe), M(iPr-N—(CH$_2$)$_2$—N-iPr)(OMe)(O$_2$CMe), M(iPr-N—(CH$_2$)$_2$—N-iPr)(OEt)(O$_2$CMe), M(iPr-N—(CH$_2$)$_2$—N-iPr)(OnPr)(O$_2$CMe), M(iPr-N—(CH$_2$)$_2$—N-iPr)(OsBu)(O$_2$CMe), M(iPr-N—(CH$_2$)$_2$—N-iPr)(OiBu)(O$_2$CMe), M(iPr-N—(CH$_2$)$_2$—N-iPr)(OtBu)(O$_2$CMe), M(Et-N—(CH$_2$)$_2$—N-Et)(OiPr)(O$_2$CMe), M(Et-N—(CH$_2$)$_2$—N-Et)(OMe)(O$_2$CMe), M(Et-N—(CH$_2$)$_2$—N-Et)(OEt)(O$_2$CMe), M(Et-N—(CH$_2$)$_2$—N-Et)(OnPr)(O$_2$CMe), M(Et-N—(CH$_2$)$_2$—N-Et)(OsBu)(O$_2$CMe), M(Et-N—(CH$_2$)$_2$—N-Et)(OiBu)(O$_2$CMe), M(Et-N—(CH$_2$)$_2$—N-Et)(OtBu)(O$_2$CMe), M(OiPr)$_2$(O$_2$CMe)$_2$, and M(OiPr)$_3$(O$_2$CMe).

* * * * *